US010413633B2

(12) United States Patent
Downes et al.

(10) Patent No.: US 10,413,633 B2
(45) Date of Patent: Sep. 17, 2019

(54) PERIPHERAL NERVE GROWTH CONDUIT

(71) Applicant: The University of Manchester, Manchester (GB)

(72) Inventors: Sandra Downes, Manchester (GB); Giorgio Terenghi, Manchester (GB); Mingzhu Sun, Manchester (GB); Paul Kingham, Umea (SE)

(73) Assignee: THE UNIVERSITY OF MANCHESTER, Manchester (GB)

( * ) Notice: Subject to any disclaimer, the term of this patent is extended or adjusted under 35 U.S.C. 154(b) by 0 days.

(21) Appl. No.: 14/885,801

(22) Filed: Oct. 16, 2015

(65) Prior Publication Data
US 2016/0082149 A1    Mar. 24, 2016

Related U.S. Application Data

(63) Continuation of application No. 13/062,234, filed on Mar. 4, 2011, now abandoned, which is a (Continued)

(30) Foreign Application Priority Data

Sep. 10, 2008    (GB) .................................. 0816574.8

(51) Int. Cl.
*A61L 27/18*    (2006.01)
*A61L 27/56*    (2006.01)
(Continued)

(52) U.S. Cl.
CPC .............. *A61L 27/18* (2013.01); *A61L 27/56* (2013.01); *A61B 17/1128* (2013.01); *A61F 2/04* (2013.01);
(Continued)

(58) Field of Classification Search
CPC ... A61F 2/0063; A61B 17/1128; A61B 17/12; A61L 27/00; A61L 2430/32
See application file for complete search history.

(56) References Cited

U.S. PATENT DOCUMENTS

| 4,534,349 A | 8/1985 | Barrows |
| 5,019,087 A | 5/1991 | Nichols |

(Continued)

FOREIGN PATENT DOCUMENTS

| EP | 1 254 671 A1 | 11/2002 |
| EP | 1 586 285 A1 | 10/2005 |

(Continued)

OTHER PUBLICATIONS

Bini et al., "Poly(1-lactide-co-glycolide) Biodegradable Microfibers and Electrospun Nanofibers for Nerve Tissue Engineering: An In Vitro Study," *Journal of Materials Science* 41(19):6453-6459, 2006.

(Continued)

*Primary Examiner* — Kathleen S Holwerda
*Assistant Examiner* — Christina C Lauer
(74) *Attorney, Agent, or Firm* — Seed IP Law Group LLP

(57) ABSTRACT

The present invention provides a peripheral nerve growth conduit for peripheral nerve repair, in particular conduits through which peripheral nerves can grow. The conduit includes poly-ε-caprolactone (PCL). Preferably, the inner (luminal) surface of the conduit comprises pits having a depth of 1-4µm. Suitably, the conduit may also include poly-lactic acid (PLA). The inner surface of the conduit may have been treated with an alkaline composition. The present invention also provides a method for treating a peripheral nerve damage using a peripheral nerve growth conduit including poly-ε-caprolactone (PCL). The present invention
(Continued)

also provides a kit for treating a peripheral nerve damage having a peripheral nerve growth conduit including poly-ε-caprolactone (PCL).

22 Claims, 16 Drawing Sheets

Related U.S. Application Data continuation of application No. PCT/GB2009/002161, filed on Sep. 9, 2009.

(51) Int. Cl.
    A61B 17/11      (2006.01)
    A61F 2/04       (2013.01)
(52) U.S. Cl.
    CPC ..... A61F 2240/001 (2013.01); A61L 2430/32 (2013.01); Y10T 156/1038 (2015.01)

(56) References Cited

U.S. PATENT DOCUMENTS

| | | | |
|---|---|---|---|
| 5,145,945 A * | 9/1992 | Tang | A61L 15/64 525/410 |
| 6,221,997 B1 * | 4/2001 | Woodhouse | C08G 18/12 528/61 |
| 7,163,545 B2 | 1/2007 | Yaszemski et al. | |
| 2001/0031974 A1 | 10/2001 | Hadlock et al. | |
| 2002/0051806 A1 | 5/2002 | Mallapragada et al. | |
| 2002/0086047 A1 | 7/2002 | Mueller et al. | |
| 2003/0176876 A1 * | 9/2003 | Chen | A61B 17/1128 606/152 |
| 2003/0204197 A1 * | 10/2003 | Onyekaba | A61B 17/1128 606/152 |
| 2004/0122454 A1 | 6/2004 | Wang et al. | |
| 2004/0266000 A1 * | 12/2004 | Offermann | A61F 2/30756 435/398 |
| 2005/0209684 A1 | 9/2005 | Alexander et al. | |
| 2006/0002978 A1 | 1/2006 | Shea et al. | |
| 2006/0085063 A1 * | 4/2006 | Shastri | A61F 2/02 623/1.41 |
| 2007/0233277 A1 | 10/2007 | Yamamoto et al. | |
| 2007/0265243 A1 * | 11/2007 | Turos | C07D 313/04 514/210.15 |
| 2007/0299510 A1 * | 12/2007 | Venkatraman | A61F 2/0077 623/1.44 |
| 2008/0109070 A1 | 5/2008 | Wagner et al. | |
| 2008/0318882 A1 * | 12/2008 | Wang | A61K 48/0075 514/44 R |
| 2009/0074832 A1 * | 3/2009 | Zussman | A61L 27/3821 424/423 |
| 2009/0275129 A1 | 11/2009 | Cooper et al. | |
| 2010/0040660 A1 | 2/2010 | Kim et al. | |
| 2010/0042206 A1 | 2/2010 | Yadav et al. | |
| 2013/0184724 A1 | 7/2013 | Downes et al. | |
| 2017/0021055 A1 | 1/2017 | Downes et al. | |

FOREIGN PATENT DOCUMENTS

| | | |
|---|---|---|
| GB | 2 386 841 A1 | 10/2003 |
| GB | 2463861 A | 3/2010 |
| GB | 2483725 A | 3/2012 |
| GB | 2490269 A | 10/2012 |
| JP | 2005-237476 A | 9/2005 |
| WO | 1996/025929 A1 | 8/1996 |
| WO | 2001/054593 A1 | 8/2001 |
| WO | 2001/081552 A1 | 11/2001 |
| WO | 2003/066705 A1 | 8/2003 |
| WO | 2004/096245 A2 | 11/2004 |
| WO | 2005/046457 A2 | 5/2005 |
| WO | 2006/044904 A2 | 4/2006 |
| WO | 2006/127712 A2 | 11/2006 |
| WO | 2007/021590 A2 | 4/2008 |
| WO | 2008/041001 A1 | 4/2008 |
| WO | 2009/094225 A2 | 7/2009 |
| WO | 2012/038691 A1 | 3/2012 |
| WO | 2015/097473 A1 | 7/2015 |

OTHER PUBLICATIONS

British Search Report under Section 17(5), dated Jan. 12, 2009, for British application No. GB0816574.8.
Caddick et al., "Phenotypic and Functional Characteristics of Mesenchymal Stem Cells Differentiated Along a Schwann Cell Lineage," *GLIA* 54:840-849, 2006.
Chew et al., "Aligned Protein-Polymer Composite Fibers Enhance Nerve Regeneration: A Potential Tissue-Engineering Platform," *Advanced Functional Materials* 17:1288-1296, 2007.
den Dunnen et al., "Light-microscopic and electron-microscopic evaluation of short-term nerve regeneration using a biodegradable poly(DL-lactide-E-caprolacton) nerve guide," *Journal of Biomedical Materials Research* 31:105-115, 1996.
den Dunnen, "Biological performance of a degradable poly(lactic acid-e-caprolactone) nerve guide: Influence of tube dimensions," *Journal of Biomedical Materials Research* 29:757-766, 1995.
Fernandez-Valle et al., "Expression of the protein zero myelin gene in axon-related Schwann cells is linked to basal lamina formation," *Development* 119:867-880, 1993.
Ferreira et al., "The ImageJ User Guide, 1.44," *U.S. National Institutes of Health*, 2011, 188 pages.
Flemming et al., "Effects of synthetic micro- and nano-structured surfaces on cell behavior," *Biomaterials* 20:573-588, 1999.
Hsu et al., "Fabrication and evaluation of microgrooved polymers as peripheral nerve conduits," *Biomedical Microdevices* 9:665-674, 2007.
Hsu et al., "Oriented Schwann Cell Growth on Microgrooved Surfaces," *Biotechnology and Bioengineering* 92(5):579-588, 2005.
International Search Report, dated Sep. 1, 2010, for PCT/GB2009/002161.
Kalbermatten et al., "Fibrin matrix for suspension of regenerative cells in an artificial nerve conduit," *Journal of Plastic, Reconstructive & Aesthetic Surgery* 61:669-675, 2008.
Kingham et al., "Adipose-derived stem cells differentiate into Schwann cell phenotype and promote neurite outgrowth in vitro," *Experimental Neurology* 207:267-274, 2007.
Mahay et al., "Schwann cell mediated trophic effects by differentiated mesenchymal stem cells," *Experimental Cell Research* 314:2692-2701, 2008.
Miller et al., "Oriented Schwann cell growth on micropatterned biodegradable polymer substrates," *Biomaterials* 22:1263-1269, 2001.
Miller et al., "Micropatterned Schwann Significantly Enhance Neurite Alignment Cell-Seeded Biodegradable Polymer Substrates and Outgrowth," *Tissue Engineering* 7(6):705-715, (2001).
Mo et al., "PCL-PGLA Composite Tubular Scaffold Preparation and Biocompatibility Investigation," *The International Journal of Artificial Organs* 29(8):790-799, 2006.
Oliveira et al., "Mesenchymal Stem Cells in a Polycaprolactone Conduit Enhance Median-Nerve Regeneration, Prevent Decrease of Creatine Phosphokinase Levels in Muscles, and Improve Functional Recovery in Mice," *Neuroscience* 170:1295-1303, 2010.
Pêgo et al., "In Vivo Behavior of Poly(1,3-Trimethylene Carbonate) and Copolymers of 1,3-Trimethylene Carbonate with D,L-Lactide or ε-Caprolactone: Degradation and Tissue Response," *Journal of Biomedical Materials Research Part A* 67(3):1044-1054, 2003.
Perego et al., "Preparation of a new nerve guide from a poly(L-lactide-co-6-caprolactone)," *Biomaterials* 15(3):189-193, 1994.
Ribeiro-Resende et al., "Strategies for inducing the formation of bands of Bungner in peripheral verve regeneration," *Biomaterials* 30:5251-5259, 2009.
Rodriguez et al., "Highly permeable polylactide-caprolactone nerve guides enhance peripheral nerve regeneration through long gaps," *Biomaterials* 20:1489-1500, 1999.

(56) References Cited

OTHER PUBLICATIONS

Rutkowski et al., "Synergistic effects of micropatterned biodegradable conduits and Schwann cells on sciatic nerve regeneration," *Journal of Neural Engineering* 1(3):151-157, 2004.
Sorensen et al., "Long-term neurite orientation on astrocyte monolayers aligned by microtopography," *Biomaterials* 28:5498-5508, 2007.
Sun et al., "Physicochemical characterization of novel ultra-thin biodegradable scaffolds for peripheral nerve repair," *Journal of Materials Sciences: Materials in Medicine* 20(5):1181-1192, 2009.
Sun et al., "Solvent-cast PCL films support the regeneration of NG108-15 nerve cells," *International Conference on Smart Materials and Nanotechnology in Engineering, Proc. of SPIE* 6423:64230E-1, 2007.
Thapa et al., "Polymers with nano-dimensional surface features enhance bladder smooth muscle cell adhesion," *Journal of Biomedical Materials Research Part A* 67(4): 1374-1383, 2003.
Tse et al., "In vitro evaluation of polyester-based scaffolds seeded with adipose derived stem cells for peripheral nerve regeneration," *Journal of Biomedical Materials Research A* 95A(3):701-708, 2010.
Wong et al., "Brain cortex regeneration affected by scaffold architectures," *Journal of Neurosurgery* 109:715-722, 2008.
Combined Search and Examination Report under Sections 17 and 18(3), for GB Application No. 1212442.6, dated Aug. 17, 2012, 6 pages.
Mobasseri et al., "Micro-structural geometry of thin films intended for the inner lumen of nerve conduits affects nerve repair," *J Mater Sci: Mater Med* 24:1639-1647, 2013.
Wang et al., "Polymers for Fabricating Nerve Conduits," *International Journal of Polymer Science*, vol. 2010, Article ID 138686, 20 pages, 2010.
British Search Report, dated Jan. 21, 2011, for British Application No. GB1015828.5, 5 pages.
de Luca, "Surface chemical modification of PCL films for peripheral nerve repair," Doctoral thesis, University of Manchester, Manchester, United Kingdom, 2012, 136 pages.
International Search Report and Written Opinion, dated Feb. 29, 2012, for International Application No. PCT/GB2011/001358, 7 pages.
International Search Report and Written Opinion, dated Mar. 3, 2015, for International Application No. PCT/GB2014/053835, 10 pages.
Reid et al., "Long term peripheral nerve regeneration using a novel PCL nerve conduit," *Neuroscience Letters* 544:125-130, 2013.
Sun et al., "Novel thin-walled nerve conduit with microgrooved surface patterns for enhanced peripheral nerve repair," *Journal of Materials Sciences: Materials in Medicine* 21(10):2765-2774, 2010.

\* cited by examiner

A

B

PERIPHERAL NERVE GROWTH CONDUIT

TECHNICAL FIELD OF THE INVENTION

The present invention relates to scaffolds for peripheral nerve repair, in particular to conduits through which peripheral nerves can grow. The present invention is also concerned with methods of making such scaffolds and of their use in the repair or growth of peripheral nerves. Furthermore, the present invention relates to methods of treating such scaffolds to enhance their suitability for use in promoting peripheral nerve repair.

BACKGROUND

The peripheral nervous system (PNS) extends outside the central nervous system (CNS) and provides the functions of, amongst other things, bringing sensory information to the CNS and receiving motor commands from the CNS, coordinating body movements and controlling the involuntary muscles. Unlike the central nervous system, the PNS is not protected by bone and is therefore vulnerable to injuries.

Damage to nerves of the PNS can cause significant motor or sensory impairment. In particular, patients with acute peripheral nerve injury usually have nerve conduction defects that can manifest as motor impairment or sensory dysfunction. Depending on the severity of the injury and the nerve affected, a severed nerve may cause paralysis, partial loss of mobility of the affected limb and/or a loss of sensation. Nerve and muscle atrophy will follow if no sufficient recovery occurs or no timely treatment is provided. Similarly, crush damage to peripheral nerves can result in reduced motor or sensory performance.

Surgical intervention is required if there is to be any prospect of repairing severed peripheral nerves. One surgical technique for attempting growth of a peripheral nerve involves providing a scaffold, usually in the form of a conduit, at the site of the nerve damage, to facilitate and encourage the extension of regenerating axons. Specifically, the scaffold is selected to provide an environment that will encourage nerve growth so that nerve function can be returned. To date, success rates for peripheral nerve growth have been low and it is presently not possible to achieve the extent of peripheral nerve growth that would be required in order to repair many of the injuries experienced by peripheral nerves. It has been suggested [1] that polyhydroxybutyrate (PHB) can be used to make peripheral nerve growth conduits, but, again, only low levels of peripheral nerve growth have been reported and the problem of repairing substantial peripheral nerve damage remains.

SUMMARY OF THE INVENTION

The present inventors have noted that in order for a peripheral nerve growth scaffold to effectively facilitate growth or repair of damaged peripheral nerves, it is desirable for the scaffold to exhibit a combination of properties.

Firstly, the material from which the scaffold is made must be not only biocompatible but also subject to in vivo degradation at a rate which is sufficiently slow to ensure adequate time for the nerve to grow through the defect gap but fast enough to ensure that the scaffold does not remain at the site of the injury such that adequate healing can occur.

Secondly, the present inventors have found that the mechanical properties of the scaffold must be such as to provide a robust and durable connection between the portions of the damaged peripheral nerve that is to be repaired (e.g. between proximal and distal stumps of a severed peripheral nerve), for example without breaking, swelling or collapsing once implanted. At the same time, the scaffold must exhibit sufficient flexibility to withstand handling and surgical implantation, as well as withstand movement experienced when in situ.

Thirdly, the present inventors have found that sufficient peripheral nerve growth is only likely to occur if the scaffold is a biocompatible substrate for nerve cells and Schwann cells. Suitably, the scaffold promotes or encourages the attachment and proliferation of peripheral nerve cells and Schwann cells; and it is desirable for the substrate to support the differentiation of nerve cells. The scaffold must therefore be non-toxic and should not release harmful break-down products. The scaffold should preferably also possess surface properties that mimic the basal lamina tissue in vivo.

Fourthly, the wall thickness of the nerve conduit should be small enough to avoid neuroma formation, rigidity and tissue compression associated with a thick wall. A thin wall, along with small device size, means less allogenic biological material and faster degradation rate.

At its most general, the present invention proposes that some or all of the above criteria can be achieved by providing a peripheral nerve growth scaffold that comprises poly-ε-caprolactone (PCL). This is based on the inventors' experiments wherein sufficient peripheral nerve regeneration occurred in a nerve conduit made from PCL.

In a first aspect, the present invention provides a peripheral nerve growth scaffold including poly-ε-caprolactone (PCL).

The present inventors have found that PCL, when provided as a scaffold, for example a conduit, surprisingly exhibits excellent mechanical properties and enhanced biocompatibility with peripheral nerve cells and Schwann cells.

Suitably, the scaffold includes at least 50 wt % PCL, based on the total weight of the scaffold. Preferably the scaffold includes at least 60 wt % PCL, more preferably at least 70 wt %, more preferably at least 75 wt % and most preferably about 80 wt % PCL. In particularly preferred embodiments, the scaffold consists essentially, preferably consists, of PCL.

The PCL as used herein can be PCL homopolymer or PCL copolymer.

If the PCL is present as a PCL copolymer, it is preferred that the PCL monomer comprises at least 50 wt % of the copolymer, based on the total weight of the polymer. Preferably at least 60 wt % of the copolymer is PCL monomer, more preferably at least 70 wt %, more preferably at least 80 wt %, and most preferably at least 90 wt %.

The present inventors have found that the mechanical properties and/or the peripheral nerve cell adhesion properties of the scaffold can be further improved if the scaffold also includes polylactic acid (PLA). Suitably, the PLA is provided as a mixture with the PCL. Alternatively, the PLA may be provided as a copolymer with PCL.

Suitably, if the PLA is provided as a copolymer, i.e. as PCL-PLA copolymer, PCL and PLA are the only comonomers. However, further comonomers can also be present.

It is preferred that the PLA is provided as a mixture (blend) with the PCL.

Preferably no more than 50 wt % of the scaffold is PLA, more preferably no more than 40 wt %, more preferably no more than 30 wt % and more preferably no more than 25 wt %. A particularly preferred concentration of PLA is about 20 wt %. This has been found to provide a good balance of mechanical and cell adhesion properties.

In this connection, if the content of PLA is greater than 50 wt %, it may be difficult or impossible to form a conduit by heat sealing (discussed below). Furthermore, if the content of PLA is greater than 50 wt %, the material is too quick to degrade in vivo.

Conversely, the presence of some PLA can improve the mechanical properties of the scaffold, in particular the flexibility of the scaffold. In addition, incorporation of PLA in combination with PCL provides improved peripheral nerve cell viability and/or proliferation. Addition of PLA in the amounts described herein also adjusts (typically increases) the rate of biodegradation of the scaffold.

Preferably the weight ratio of PCL:PLA is in the range 20:1 to 1:1. More preferably the ratio is in the range 10:1 to 2:1, more preferably 7:1 to 2:1, more preferably 6:1 to 2:1 and most preferably 5:1 to 3:1. A particularly preferred ratio is about 4:1.

The term "PCLA" is used herein to denote a combination of PCL and PLA. PCLA can be a mixture (blend) of PCL and PLA, or a PCL-PLA copolymer.

Suitably the PCL has a number average molecular weight (Mn) in the range 10,000 to 200,000. Preferably the Mn is in the range 20,000 to 140,000, more preferably 40,000 to 120,000 and most preferably 60,000 to 100,000. A particularly preferred Mn is about 80,000.

Suitably the PLA, if present, has a number average molecular weight (Mn) in the range 10,000 to 100,000. Preferably the Mn is in the range 10,000 to 80,000, more preferably 10,000 to 50,000 and most preferably 20,000 to 40,000. A particularly preferred Mn is about 30,000.

Suitably the scaffold is a conduit. Suitably, the conduit provides a luminal space in which peripheral nerve cells can grow (e.g. regenerating nerve fibres can grow inside the conduit, suitably in the lengthwise direction of the conduit). Typically a conduit wall surrounds and defines the luminal space.

Suitably the conduit is tubular. Preferably the conduit has tubular conduit walls. Suitably, the tubular conduit walls surround and define a substantially cylindrical luminal space.

Suitably, the conduit has a circular cross section.

Preferably the conduit is substantially straight. However, the conduit can also be bent or curved.

Preferably the thickness of the conduit walls is in the range 10 µm to 300 µm. Preferably the conduit walls have a thickness in the range 10 µm to 200 µm, more preferably 10 µm to 100 µm, more preferably 20 µm to 100 µm, more preferably 20 µm to 80 µm and most preferably 55 µm to 65 µm. A particularly preferred thickness is about 60 µm.

The present inventors have found that a conduit wall thickness as described above provides a good balance between degradation time, mechanical strength and flexibility.

Suitably the length of the scaffold, e.g. the conduit, is selected to be appropriate to the nerve damage that is to be repaired. For example, if the peripheral nerve damage comprises a severed peripheral nerve with 10 mm of the peripheral nerve missing, then the length of the scaffold will be chosen so as to be sufficient to bridge the gap in the peripheral nerve. Typically, the conduit will be longer (e.g. 10% to 50% longer) than the gap.

Typically, the scaffold has a length in the range 5 mm to 50 mm, more preferably 5 mm to 30 mm, most preferably 5 mm to 20 mm.

As with the length of the scaffold, the width, e.g. diameter, of the scaffold is selected so as to be appropriate to the peripheral nerve damage that is to be repaired. Suitable diameters are in the range 1 to 5 mm.

Preferably the scaffold is made from a film comprising PCL. The present inventors have found that film formation can provide control over mechanical and cell adhesion properties.

Typically the film is formed by solvent evaporation. That is, it is preferred that a film comprising PCL is formed by dissolving or dispersing the PCL in a solvent, casting the resultant solution or dispersion onto a surface and allowing the solvent to evaporate.

The present inventors have found that halogenated solvents are particularly effective for film formation. Naturally, the solvent should suitably be a liquid at room temperature. In particular, halogenated hydrocarbon solvents have been found to work well, especially halogenated alkanes (haloalkanes), alkenes, benzene and toluene. Particularly preferred are halogenated $C_{1-10}$ alkanes and alkenes.

Chlorinated solvents are particularly preferred. Chloro-substituted $C_{1-4}$ alkanes especially chloro-substituted methane, is especially preferred.

The most preferred solvents are dichloromethane (DCM) and chloroform. DCM is particularly preferred. The present inventors have found that DCM permits good control over the properties of the film. In particular, the present inventors have found that the surface morphology of the film is controllable with DCM such that cell adhesion, for example, can be enhanced as compared to other solvents. The surface morphology of the scaffold is discussed below.

Suitably the solvent is heated, for example to a temperature in the range 40-60° C. This may assist in dissolving the PCL.

Preferably the concentration of the PCL in the solvent is in the range 1 to 10% (wt/vol), more preferably 1 to 5%, and most preferably 2 to 4%. A particularly preferred concentration is about 3%.

Preferably the film is cast onto a smooth surface, for example glass surface. The smooth surface can be provided by a glass slide for example. Suitably the surface is degreased prior to casting.

Suitably the film is allowed to dry in air. Optionally, air flow is provided to facilitate evaporation of the solvent. The present inventors have found that controlled evaporation of the solvent produces the most desirable surface properties. Suitably, the solvent is allowed to evaporate for at least 24 hours, preferably at least 48 hours. Preferably, film drying/solvent evaporation occurs at room temperature.

Typically, after solvent evaporation has been completed, the film is washed. Suitable washing agents include water, preferably distilled water.

Preferably the film is sterilised, for example sterilised using UV radiation, γ radiation or 70% ethanol. Indeed, any suitable known technique for sterilising can be used.

The present inventors have found that the advantageous properties of a scaffold comprising PCL can be further improved by treating at least one surface of the scaffold with an alkaline composition. Preferably this is achieved by treating the surface prior to formation of the scaffold. In embodiments, a film is treated with an alkaline composition prior to forming a conduit from the film.

Preferably treatment with an alkaline composition includes exposing the surface to an alkaline composition. A preferred alkaline composition includes hydroxide. Suitably the alkaline composition is an aqueous solution. A particularly preferred composition is aqueous NaOH.

The strength (and hence alkalinity) of the alkaline composition can be adjusted so as to provide the desired surface modifying effect. In the case of NaOH, a concentration in the range 1N to 20N is preferred, with 5N to 15N being particularly preferred, and 8N to 12N being yet more preferred. In embodiments, a concentration of 10N is used.

The duration of the treatment can similarly be adjusted to provide the desired surface modifying effect. However, a duration of 30 minutes to 3 hours is preferred, with 30 minutes to 2 hours being more preferred and 45 minutes to 90 minutes being even more preferred. In embodiments, the treatment time is about 60 minutes.

Suitably, the surface of the scaffold that is treated is a surface that in use is exposed to a peripheral nerve growing volume. In other words, preferably the surface is a surface to which it is desired that peripheral nerve cells adhere and/or proliferate.

In the case of the scaffold being a conduit, the surface is preferably a luminal surface of the conduit (i.e. an inward facing surface).

Without wishing to be bound by theory, the present inventors believe that alkali treatment of the scaffold causes ester hydrolysis of the PCL. Suitably this causes formation of —COOH and/or —OH terminated PCL chains. Thus, ester hydrolysis suitably occurs as a result of alkali treatment. The present inventors believe that the presence of the hydrolysed ester (and in particular the —COOH and/or —OH moieties) may be, at least in part, responsible for the observed enhancement of cell adhesion and/or cell proliferation.

Furthermore, the present inventors have found that treatment with an alkaline composition can increase the hydrophilicity of the surface. Suitably this in turn enhances the attachment of peripheral nerve cells. This increase in hydrophilicity is demonstrated by an increase in the wettability of the surface.

In addition, the present inventors have observed that the surface morphology of the surface can also change as a result of treatment. For example, a change in the size of pits in the surface may occur. Suitably, treatment with an alkaline composition reduces the surface roughness (Ra) of the surface.

Furthermore, the present inventors have found that treatment with an alkaline solution can also provide accelerated degradation of the scaffold in vivo.

Preferably after treatment with an alkaline composition, the surface is washed. Suitably the washing step removes residual alkali. Suitably the washing step returns the pH of the surface to neutral. Preferably water (especially distilled water) is used to wash the surface.

Preferably the scaffold is provided as a conduit. Suitably the conduit is formed from a film. Suitably this is achieved by bringing two opposite edges of the film together, preferably by rolling the film up. Typically the film is rolled around a conduit forming member. Suitably this provides the desired dimensions (e.g. diameter) of the conduit. The conduit forming member can be a cannula or other suitably dimensioned structure (e.g. a mandrel).

In embodiments, the conduit is formed from more than one film. For example, a plurality of films may be rolled up to provide a laminate structure (e.g. a conduit wall comprising a plurality of layers of film).

Suitably the edges of the film are fixed together. Preferably this is achieved by heat sealing the film in its rolled up state. For example, the rolled up film (suitably on the conduit forming member) is heat sealed. Preferably heat sealing is achieved using a hot plate, but other heat sources could be used. Thus, the conduit is suitably formed by rolling up a film and heat sealing the edges of the film. Suitably heat sealing occurs at a temperature in the range 50-100° C., for example about 60° C. In practice, the heat sealing temperature is selected based on the melting temperature (Tm) of the material. Melting temperature can be measured by DSC, for example. Other fixing methods can also be used. However, heat sealing is preferred, not least because the present inventors have found that the surface morphology of the film is maintained after heat treatment. A further advantage of this approach is that no other potentially toxic materials (e.g. super glue) are introduced to this system by using the heat sealing method.

Suitably the "air" side of the film (i.e. the side not in contact with the glass surface) becomes the luminal or inner surface of the conduit.

The surface of the scaffold that in use is exposed to a peripheral nerve growth volume is referred to herein as the inner surface of the scaffold (e.g. the inner or luminal surface of a conduit).

Preferably the inner surface of the scaffold comprises pits.

Preferably the pits have an average diameter in the range 1-20 µm. Suitably the average diameter is in the range 1-15 µm, preferably 1-10 µm. Other preferred ranges are 2-15 µm, more preferably 2-12 µm and most preferably 3-10 µm.

Pit dimensions are measured in accordance with the method described herein.

Preferably the pits have an average depth in the range 0.5-8 µm. Suitably the average depth is in the range 1-6 µm, preferably 1-5 µm and most preferably 1-4 µm.

Suitably the % coverage of the pits on the inner surface is the range 20% to 80%, preferably 30% to 70%, more preferably 40% to 60% and most preferably 45% to 55%. A particularly preferred % coverage is about 50%. Measurement of % coverage is discussed below.

Preferably the surface is the luminal surface of a conduit.

Suitably, the pits on the surface are formed by film formation as described herein. In particular, the present inventors have found that film formation using DCM provides a particularly desirable distribution and/or size of pits.

Preferably the inner surface has an average surface roughness (Ra) of at least 1 µm, more preferably at least 2 µm, more preferably at 2.5 µm and most preferably at least 2.75 µm. Suitably the average surface roughness is no more than 5 µm. Measurement of average surface roughness is discussed below.

Preferably the scaffold comprises a surface which in use is not exposed to a peripheral nerve growth volume. This is referred to herein as the outer surface of the scaffold (e.g. the outer surface of a conduit). Preferably, in the case where the scaffold is formed from a film, the outer surface is the surface of the film that was in contact with the surface on which the film was cast (e.g. a glass surface).

Suitably the outer surface is substantially free of pits. However, if such pits are present, preferably they have an average diameter in the range 1-5 µm. Suitably the average diameter is in the range 1-3 µm.

Suitably, if pits are present on the outer surface, they should have a small depth, preferably an average depth of less than 1 µm, more preferably less than 0.75 µm, more preferably less than 0.5 µm.

The present inventors have found that it is desirable for the outer surface to be smoother than the inner (luminal) surface. Thus, suitably, the surface roughness of the inner surface of the scaffold (e.g. conduit) is greater than the surface roughness of the outer surface.

In particular, the present inventors have found that a low density of pits on the outer surface is desirable.

Preferably the inner surface of the scaffold (e.g. a conduit) includes nanopits, suitably the nanopits have a depth in the range 50-800 nm, preferably 50-500 nm. Suitably these nanopits are in addition to the pits discussed above.

Suitably the scaffold is made using a film and the nanopits are formed during film formation. In particular, the nanopits may be formed during solvent evaporation from the film. Alternatively or additionally, the nanopits may be formed by alkaline treatment (e.g. NaOH treatment).

Preferably the outer surface has an average surface roughness (Ra) of less than 2 µm, more preferably less than 1.5 µm, more preferably less than 1 µm and most preferably less than 0.5 µm.

Preferably the surface roughness of the outer surface is less than the surface roughness of the inner surface. Suitably, the difference between the surface roughness of the inner surface and the outer surface is at least 0.5 µm, preferably at least 1 µm, and most preferably at least 1.5 µm.

When the scaffold is a conduit, it is preferred that the conduit wall does not include any pores extending through the thickness of the wall (through holes). This arrangement has been found to provide advantages because it prevents the escape of the regenerating axons from the conduit. It may also prevent ingrowth of fibrous tissues which can lead to unwanted scarring. This may assist in providing a controlled environment within the conduit for nerve repair.

However, a small number of such pores can be present, for example no more than 5% of the surface area comprises such pores. Preferably no more than 2% and more preferably no more than 1% of the surface area comprises such pores. Suitably, if such pores are present, they have a diameter not larger than 15 µm. Preferably they have a diameter in the range 1-10 µm. If present, these pores can assist in avoiding the building up of pressure resulting from fluid retention.

Preferably the film used to form the scaffold has a tensile strength of at least 5 MPa, more preferably at least 8 MPa, more preferably at least 10 MPa and most preferably at least 15 MPa.

Preferably the film used to form the scaffold has a Young's modulus of at least 80 MPa, more preferably at least 100 MPa, more preferably at least 110 MPa and most preferably at least 120 MPa. Preferably the Young's modulus is no more than 200 MPa and more preferably no more than 180 MPa.

Preferably the film used to form the scaffold has a maximum strain of at least 1 mm/mm.

Preferably the scaffold is flexible. In embodiments, the present inventors have found that the PCL scaffold is highly flexible. This flexibility reduces or avoids irritation to surrounding tissues.

In particular, the present inventors have found that a scaffold comprising PCL provides an excellent combination of mechanical properties, making it suitable for handling by a surgeon, whilst providing a surprisingly effective surface environment for peripheral nerve growth.

Preferably the scaffold is used to treat peripheral nerve damage.

Peripheral nerve damage can be a gap in a peripheral nerve, i.e. a severed peripheral nerve. Alternatively or additionally, peripheral nerve damage can be a partially severed peripheral nerve. Alternatively or additionally, peripheral nerve damage can be a crushed peripheral nerve.

Suitably the scaffold provides a microenvironment at the injured site with protecting and promoting effects for the regenerating peripheral nerve. For example, it can prevent the infiltration of fibroblasts and the escape of regenerating neurites; at the same time it can contain endogenous growth factors in situ. Therefore, the scaffold is suitable for treating crushed/damaged peripheral nerves as well as severed peripheral nerves.

In particular, the scaffold of the present invention can be used to treat neurapraxia (nerve nonfunction), axonotmesis (axon cutting), and neurotmesis (nerve cutting).

It is envisaged that the scaffold of the present invention is used to treat some or all of these types of peripheral nerve damage.

It particular, the scaffold is preferably used to treat acute peripheral nerve injury.

The peripheral nerve damages can occur as a result of accidental injury, disease or surgical procedures. For example, peripheral nerve damage can occur as a result of a cut to the hands or feet, crush injuries, organ transplant, tumour removal, congenital birth defects or previous attempts to repair peripheral nerves.

The scaffold of the present invention can be used to repair peripheral nerve damage wherever it occurs in the body. Examples of peripheral nerves that are most frequently damaged include: palmar digital nerves, median nerves, the ulnar nerve and the radial nerve. Further examples include the brachial plexus and musculocutaneous nerves. Yet further examples (in the lower limbs) include plantar digital nerve, peroneal and the sciatic nerve.

In embodiments, the scaffold is used to enclose the affected part of the peripheral nerve (i.e. the damaged portion).

In other embodiments wherein the peripheral nerve damage includes a severed peripheral nerve such that there is a gap in the peripheral nerve, the scaffold is positioned so as to bridge the gap between the respective proximal and distal ends of the severed nerve. In preferred embodiments wherein the scaffold is a conduit, the conduit is positioned so as to provide a guide for peripheral nerve growth between the axial and distal ends of the severed nerve.

The scaffold can be attached to the peripheral nerve by any means known to the skilled reader. Suitably the scaffold is attached using a suture. Suitably the suture provides attachment between the epineurium and the scaffold. Bio-glue can also be used.

The scaffold can be used to treat peripheral nerve damage in an animal, including humans and non-humans. Treatment of humans is particularly preferred.

To assist in the treatment of peripheral nerve damage, the scaffold may be used in conjunction with a peripheral nerve cell growth medium (e.g. a gel matrix). Suitably the peripheral nerve cell growth medium includes one or both of growth factors and Schwann cells/differentiated stem cells. Suitably the peripheral nerve cell growth medium is a transport media for cells and/or growth factors (i.e. the peripheral nerve cell growth medium is, or comprises, a transport matrix). Typically the peripheral nerve cell growth medium is a hydrogel.

In use, the peripheral nerve cell growth medium (e.g. a gel matrix) is preferably introduced into the scaffold in situ. Typically the scaffold is positioned at the site of the peripheral nerve damage (e.g. after suturing) and then the growth medium (gel matrix) may be delivered to the scaffold. In preferred embodiments wherein the scaffold is a conduit, suitably the growth medium is delivered into the luminal volume of the conduit, optionally together with cells and/or growth factors. Suitably this is achieved by injecting the growth medium, for example through the end of the conduit after suturing.

While the invention has been discussed above in relation to a scaffold, the present invention also provides methods and uses relating to the scaffold.

In a further aspect, the present invention provides a peripheral nerve growth conduit, wherein the conduit includes poly-ε-caprolactone.

In a further aspect, the present invention provides a peripheral nerve growth conduit, wherein the conduit includes poly-ε-caprolactone and polylactic acid.

In a further aspect, the present invention provides a peripheral nerve growth conduit, wherein the conduit is prepared using solvent evaporation method wherein the solvent comprises a halogenated solvent, preferably dichloromethane or chloroform.

In a further aspect, the present invention provides a peripheral nerve growth scaffold, wherein at least part of the surface of the scaffold has been treated with alkali.

In a further aspect, the present invention provides a peripheral nerve growth scaffold, wherein at least one surface of the scaffold includes —COOH and —OH groups.

In a further aspect, the present invention provides a peripheral nerve growth scaffold, wherein one surface of the scaffold includes pits having an average diameter in the range 1-15 μm.

In a further aspect, the present invention provides a peripheral nerve growth scaffold, wherein one surface of the scaffold includes pits having an average depth in the range 1-5 μm.

In a further aspect, the present invention provides a peripheral nerve growth conduit, wherein the surface roughness of the inner surface of the conduit is greater than the surface roughness of the outer surface.

In a further aspect, the present invention provides a peripheral nerve growth conduit, wherein the thickness of the wall of the conduit is in the range 20-100 μm.

In a further aspect, the present invention provides a kit for treating a peripheral nerve in a human or animal, the kit including a peripheral nerve growth scaffold according to any one of the preceding claims.

Preferably, the kit includes the peripheral nerve growth scaffold in a sterilised package.

Preferably, the kit includes a plurality of peripheral nerve growth scaffolds as described herein. More preferably, the peripheral nerve growth scaffolds vary in size according to one or more of the following dimensions: scaffold length, scaffold internal diameter and scaffold wall thickness. A user may then select the correct size of nerve repair scaffold from the kit to suit the requirements of a particular nerve repair treatment. Suitably, each peripheral nerve growth scaffold in the kit is in an individual sterilised package.

In a further aspect, the present invention provides use of poly-ε-caprolactone (PCL) in a peripheral nerve growth scaffold.

In a further aspect, the present invention provides use of hydroxide to treat the surface of a peripheral nerve growth scaffold including poly-ε-caprolactone (PCL). Suitably the action of the hydroxide encourages growth of peripheral nerves on said surface.

In a further aspect, the present invention provides use of PCL for the manufacture of a peripheral nerve growth scaffold for treatment of a damaged peripheral nerve.

In a further aspect, the present invention provides PCL for use in treating a damaged peripheral nerve.

In a further aspect, the present invention provides PCLA for use in a method of treatment of the human or animal body.

In a further aspect, the present invention provides PCLA for use in treating a damaged peripheral nerve.

In a further aspect, the present invention provides a method of treating a damaged peripheral nerve using PCLA.

In a further aspect, the present invention provides a method of treating a damaged peripheral nerve using a peripheral nerve growth scaffold including PCL.

In a further aspect, the present invention provides a method of treating a severed peripheral nerve, the method including the steps of
(i) providing a peripheral nerve growth scaffold including PCL,
(ii) coupling a first severed end of the nerve to a first portion of the scaffold, and
(iii) coupling a second severed end of the nerve to a second portion of the scaffold,
wherein the first and second portions of the scaffold are separated by a growth portion of the scaffold having a growth surface on which at least one of the first and second severed ends of the nerve is able to grow in a direction towards the respective other severed end.

Suitably the first severed end is the proximal end of the nerve and the second severed end is the distal end of the severed nerve.

Any one or more of the aspects of the present invention may be combined with any one or more of the other aspects of the present invention. Similarly, any one or more of the features and optional features of any of the aspects may be applied to any one of the other aspects. Thus, the discussion herein of optional and preferred features may apply to some or all of the aspects. In particular, optional and preferred features relating to the scaffold, methods of making the scaffold and methods of using the scaffold, etc apply to all of the other aspects. Furthermore, optional and preferred features associated with a method or use may also apply to a product (e.g. scaffold) and vice versa.

BRIEF DESCRIPTION OF THE DRAWINGS

Embodiments of the invention and experiments illustrating the advantages and/or implementation of the invention are described below, by way of example only, with respect to the accompanying drawings, in which.

DETAILED DESCRIPTION OF THE INVENTION

Definitions

The term "scaffold" as used herein is well known to the skilled reader. In particular, a scaffold in the context of the present invention is a structure adapted for peripheral nerve growth. Suitably the scaffold promotes or enhances peripheral nerve growth.

The term "pit" as used herein means a closed-end pore or "blind" hole. In short, a "pit" as used herein does not extend all of the way through the wall of the scaffold.

The term "nanopit" as used herein means a pit having at least one dimension on the nano- or sub-μm scale.

Film Formation

PCL pellets (Sigma-Aldrich) were dissolved in dichloromethane (3.0%, wt/v) and gentle heating at a temperature of approximately 50° C. could be used to assist dissolving. PCL solution was evenly applied onto borosilicate glass slides (75×25 mm²), which had been degreased with acetone/ethanol (1:1, v/v).

Complete solvent evaporation was allowed in a fume cupboard for at least 48 hours, to provide films with a thickness of 60±5 μm.

The polymer films were washed in distilled H₂O and sterilized by UV irradiation for 1 hour prior to in vitro and in vivo testing.

Complete solvent evaporation was confirmed by FTIR (Thermo Nicolet Nexus™ FTIR (Cambridge, UK) controlled by OMNIC Software Version 6.1a), which ensured that no solvent toxic effect would occur in the subsequent cell growth and in vivo testing.

Using the same method, a mixture of PCL and PLA was formed as a film (the "PCLA film"). The weight ratio of PCL to PLA was 4:1.

Alkaline (Hydroxide) Treatment

PCL films were soaked in 10N NaOH for 1 hour with horizontal shaking at 150 rpm at room temperature and then rinsed thoroughly with distilled H₂O to return the pH to neutral (pH 7.2-7.4). Subsequent XPS analysis (discussed below) confirmed the cleavage of the ester bond (ester hydrolysis) as follows:

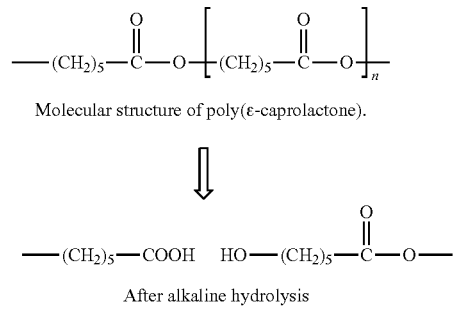

Molecular structure of poly(ε-caprolactone).

⇓

—(CH₂)₅—COOH    HO—(CH₂)₅—C(=O)—O—

After alkaline hydrolysis

For comparison, a film of PHB was treated with NaOH. However, the PHB film did not withstand NaOH treatment; it was too brittle and shattered into pieces.

Conduit Formation

Figure 1:
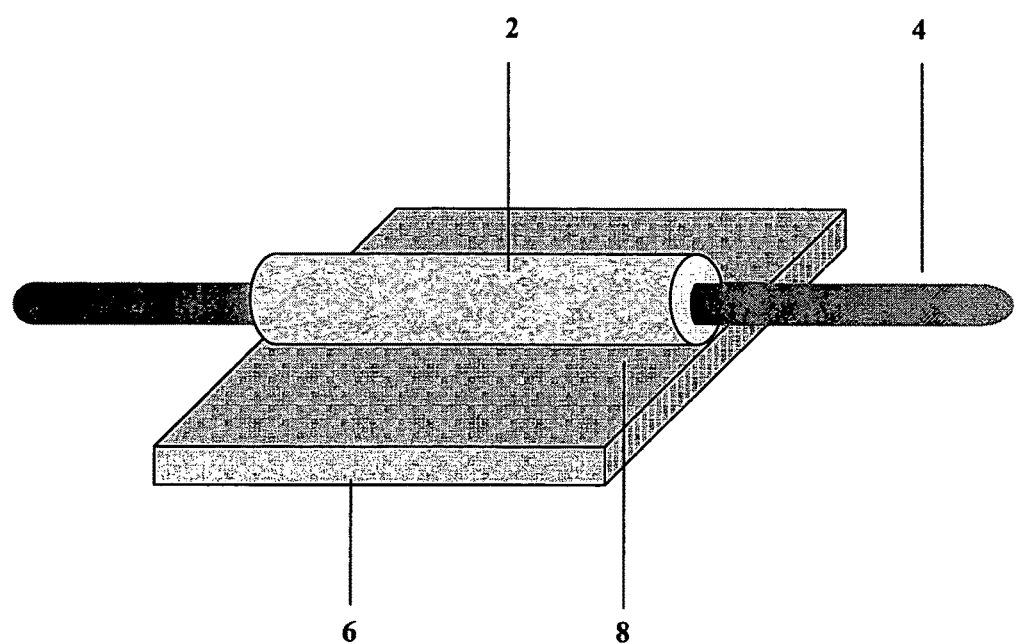
FIG. 1 shows schematically the heat sealing method preferred for forming the conduit of the present invention.

FIG. 1 illustrates schematically the methodology used to form the PCL and PCLA conduits. The films 2 were wrapped around a 16G cannula 4, to form a tubular conduit. Sealing of the overlapping edges of the film was carried out by briefly (several seconds) pressing the edges on to a hot plate 6 at 60° C. A thin layer of tin foil was provided (at location 8) between the outer surface of the conduit and the hot plate. This provided a durable seal and the resultant tubular conduit was self supporting.

The inner (luminal) surface of the PCL and PCLA conduits was unchanged as a result of the heating step.

Surface Analysis—AFM & SEM

PCL and PCLA films prepared as described above were imaged using Atomic Force Microscopy (AFM, Veeco CP II) and Philips XL30 Field Emission Gun Scanning Electron Microscopy (SEM) techniques. 3-D images were created, and dimension of individual pores measured using IP Image Analysis 2.1 software (Image Processing and Data Analysis version 2.1.15. TM Microscopes, copyright 1998-2001).

Figure 2:
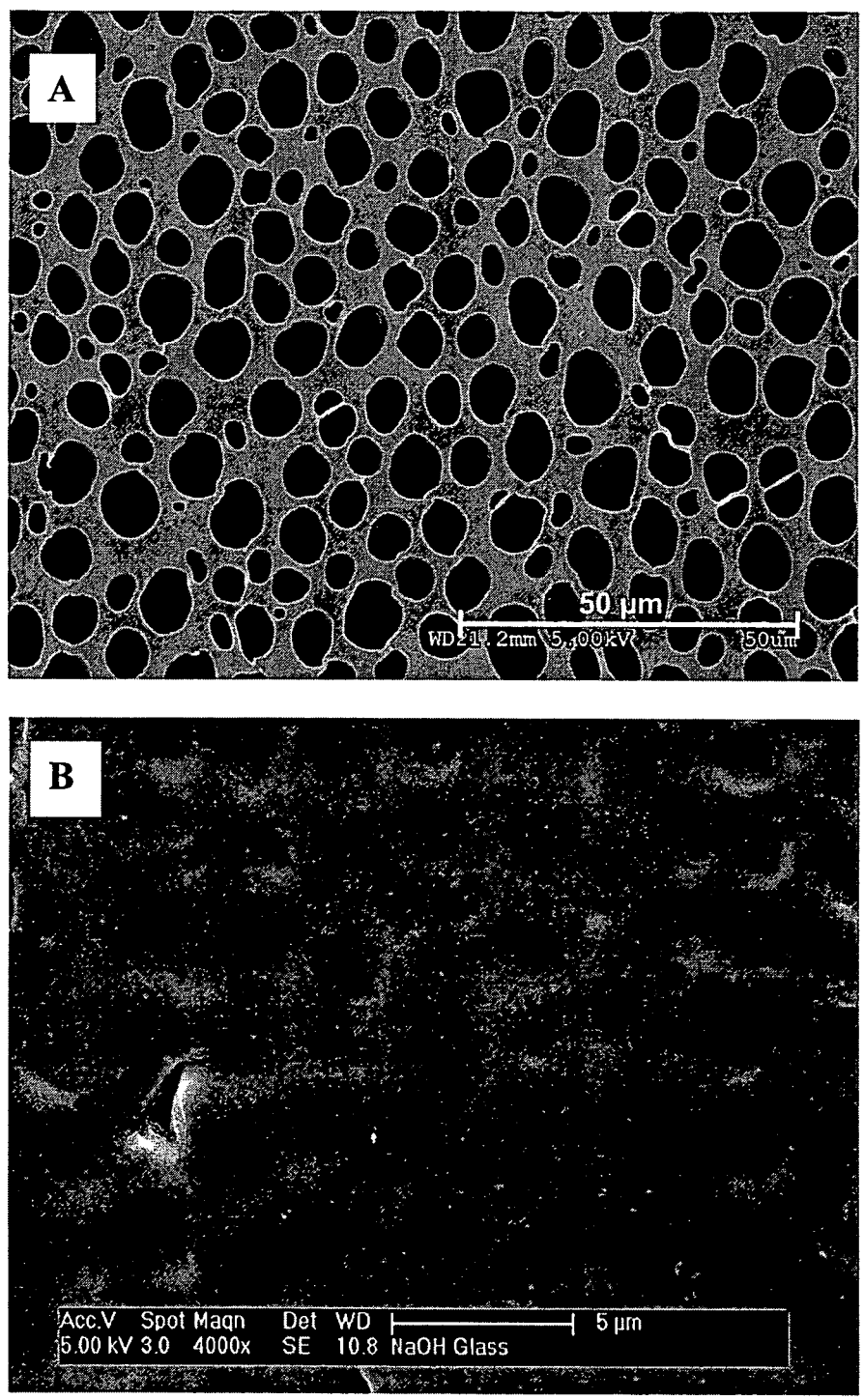
FIG. 2 shows SEM images of the air (inner) (2A) and glass (outer) (2B) surfaces of a PCL film.

FIG. 2A shows an SEM image of the PCL film, being the "air" surface of the film that is destined to become the inner (luminal) surface of the conduit.

FIG. 2B shows an SEM image of the "glass" surface of the film, which when formed as the conduit will be the outer surface.

It is clear from FIGS. 2A and 2B that the outer surface is considerably smoother (i.e. has a lower surface roughness) than the inner surface. In particular, FIG. 2A shows that the inner surface is pitted and that the plurality of pits have diameters in the range 1 to 10 μm. FIG. 2B shows that the outer surface has smaller and shallower pits.

Indeed, SEM imaging revealed that PCL films comprised pits on the air surface in the range of 1-10 μm in diameter; the depth of these pits was between 1-5 μm. The glass (outer) surface was also pitted, with pores in the diameter of 1-5 μm. However, the depth of pits on this side of the films was down to 100 nm-800 nm.

The diameter and depth of the pits for the inner surface of both PCL and PCLA films are set out in Table 1. Also included is diameter and depth data for the same surfaces after treatment with NaOH.

TABLE 3

Inner surface pit size of PCL and PCLA films.

| Samples | Pore diameter (μm) | Pore depth (μm) |
|---|---|---|
| PCL | 1-10 | 1-5 |
| PCL (NaOH treated) | 1-10 | 1-5 |
| PCLA | 1-8 | 1-3 |
| PCLA (NaOH treated) | 1-8 | 1-3 |

The results in Table 1 show that NaOH treatment didn't affect the overall morphology of the materials but that some reduction in the surface roughness was observed. In addition, the results show that PCLA films have smaller pit size than PCL films.

The % coverage of pits on the inner surface is 51%, measured using SEM image and data and Image J software [2].

Figure 3:
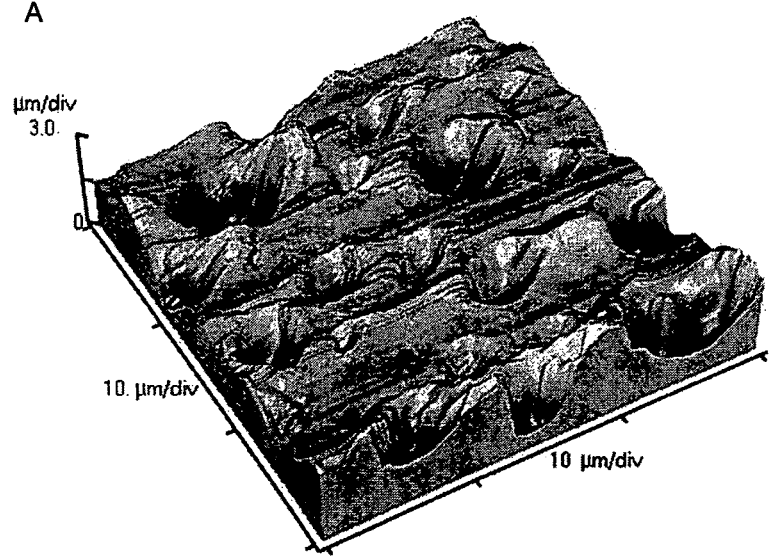
FIG. 3 shows 3-D AFM images of the air (inner) (3A) surfaces and glass surface (outer) (3B) of a PCL film.
Figure 3:
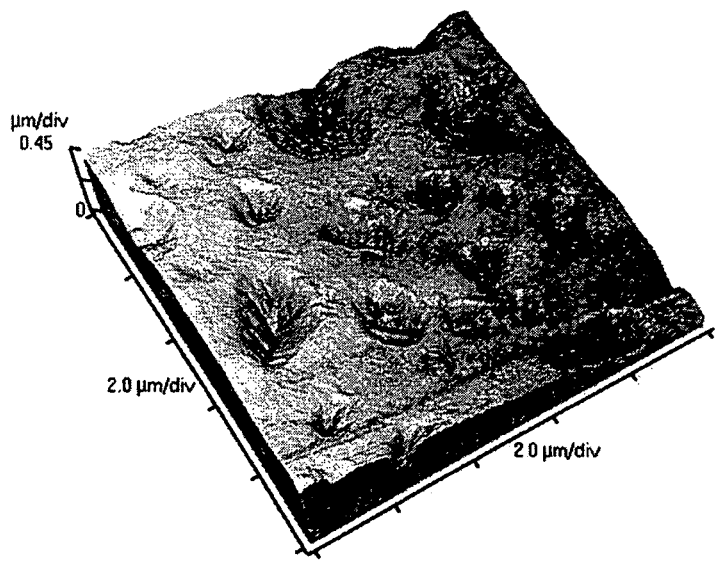

The 3-D image generated from AFM data of the PCL film inner ("air") and outer ("glass") surfaces are shown in FIG. 3. The scanned area of 3A is 30×30 μm$^2$; for 3B it is 10×10 μm$^2$. The pits ("closed end" holes) can be seen clearly.

The average surface roughness (Ra) of the untreated inner surface is 3.883 μm, and of the NaOH treated surface is 3.041 μm.

The average surface roughness (Ra) of the outer surface is 0.569 μm and 0.576 μm respectively before and after NaOH treatment.

The average surface roughness (Ra) and pit size were measured using AFM images and IP Image Analysis 2.1 software.

Figure 4:
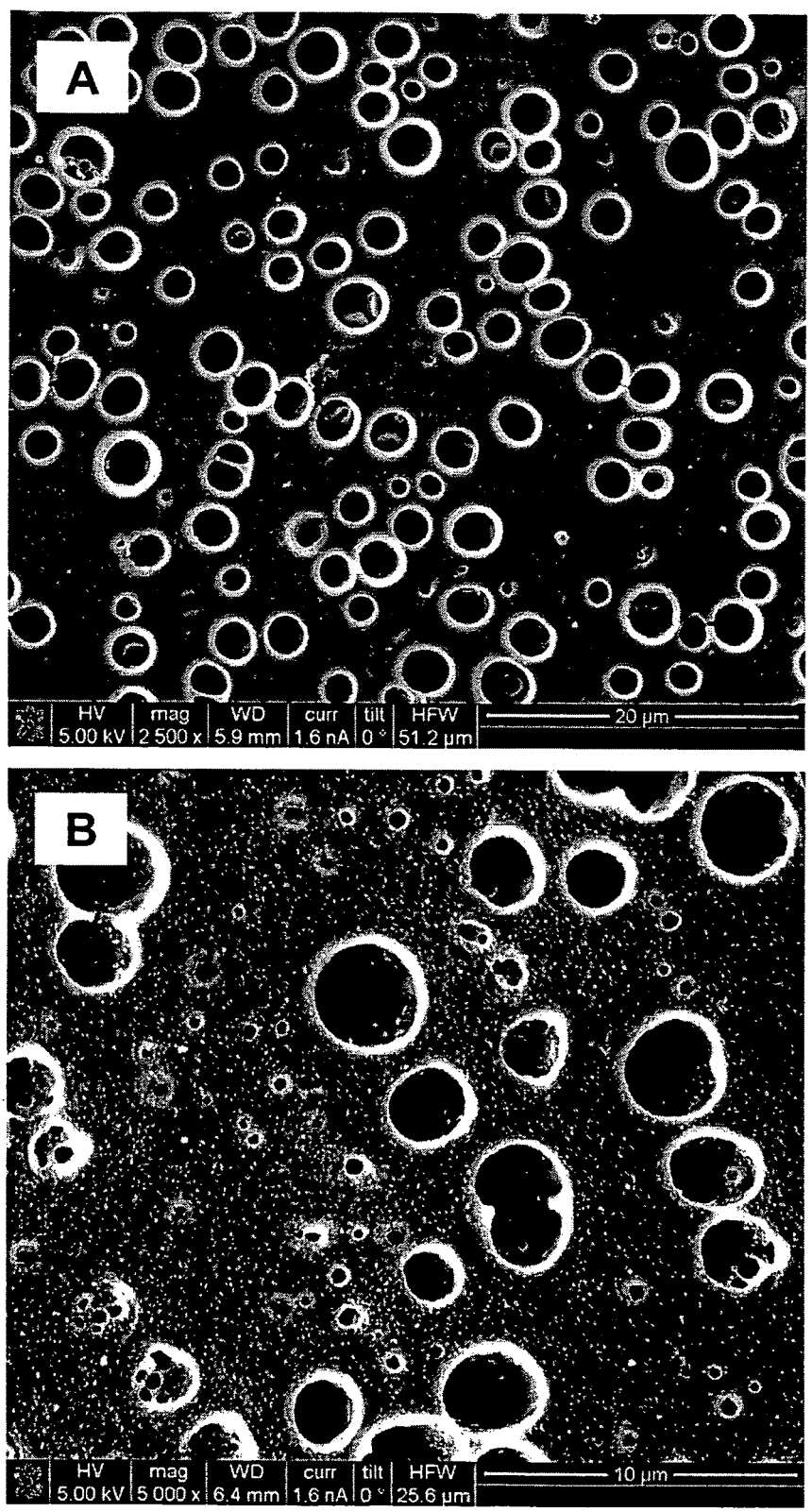
FIG. 4 shows SEM images of a cast PCLA film before (4A) and after (4B) NaOH treatment.

FIG. 4, being SEM images of a PCLA film before (4A) and after (4B) treatment with NaOH, shows that the pitted morphology is maintained after treatment. Nanoscale structure (nanopits) can also be seen in 4B indicating that NaOH treatment causes formation of nanopits.

Measurement of % coverage of pits using Image J software [2] and SEM image data showed that the % coverage of pits for the PCL film is 51%, and for the PCLA film it is 35.8%. In addition, the size of the pits on the PCLA film is smaller than that for the PCL film.

Surface Analysis—XPS

X-ray Photoelectron Spectroscopy (XPS, AXIS Ultra) was used to analyse the chemical and electronic state of the carbon and oxygen elements existing in the PCL film before and after treatment with NaOH.

Figure 5:
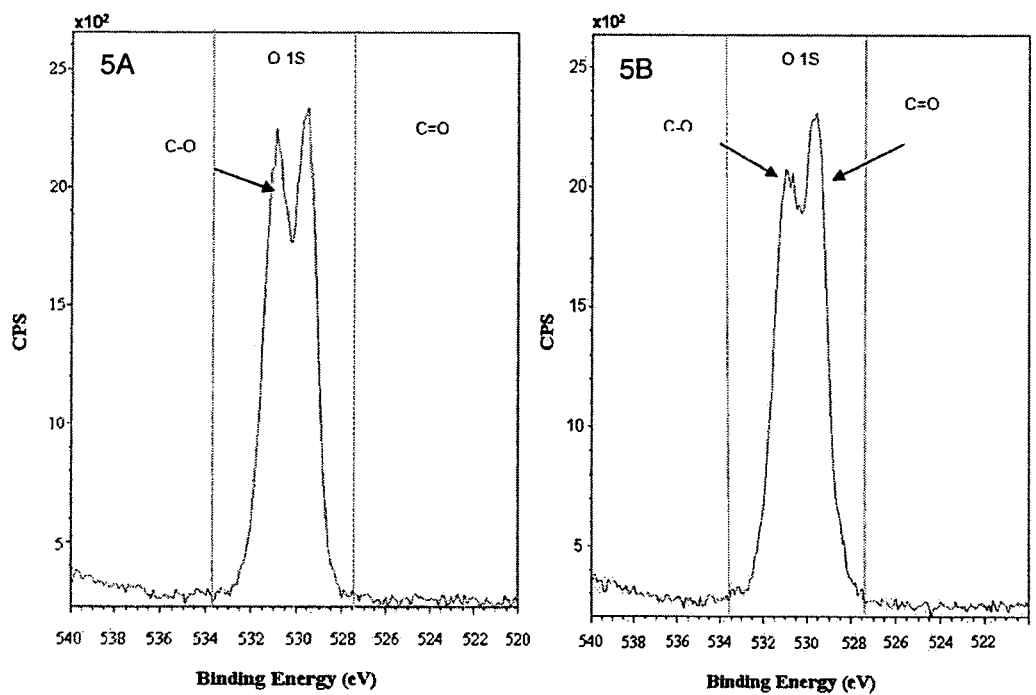
FIG. 5 shows XPS spectra for dichloromethane cast PCL films before (5A) and after (5B) NaOH treatment.

FIG. 5 shows XPS spectra for a PCL film before (5A) and after (5B) NaOH treatment. The reduced peak of C—O group confirms that alkaline hydrolysis has cleaved the ester bond.

Wettability

The hydrophilicity of the PCL and PCLA films before and after NaOH treatment was compared by measuring the static contact angles using Krüss DSA 100 Drop Size Analyser. Ten treated or untreated films were tested and five randomly selected areas were measured on each film. A glass coverslip was tested for comparison. The results are reported in Table 2 below, where "—OH" denotes NaOH treatment.

TABLE 2

Water contact angle for PCL and PCLA films ("S" designates smooth outer surface; "P" pitted inner (luminal) surface)

| Samples | Water Content Angle (%) | Standard Deviation (%) |
|---|---|---|
| PCL-OH-S | 36.7 | 4.65 |
| PCL-OH-P | 52.79 | 10.8 |
| PCL-S | 43.81 | 6.3 |
| PCL-P | 64.58 | 2.8 |
| PCLA-OH-S | 61.49 | 4.6 |
| PCLA-OH-P | 74.45 | 9.2 |
| PCLA-S | 69.36 | 4.2 |
| PCLA-P | 76.63 | 6.5 |
| PLA-P | 71.33 | 3.3 |
| Glass Coverslips | 31.25 | 9.87 |

Figure 6:
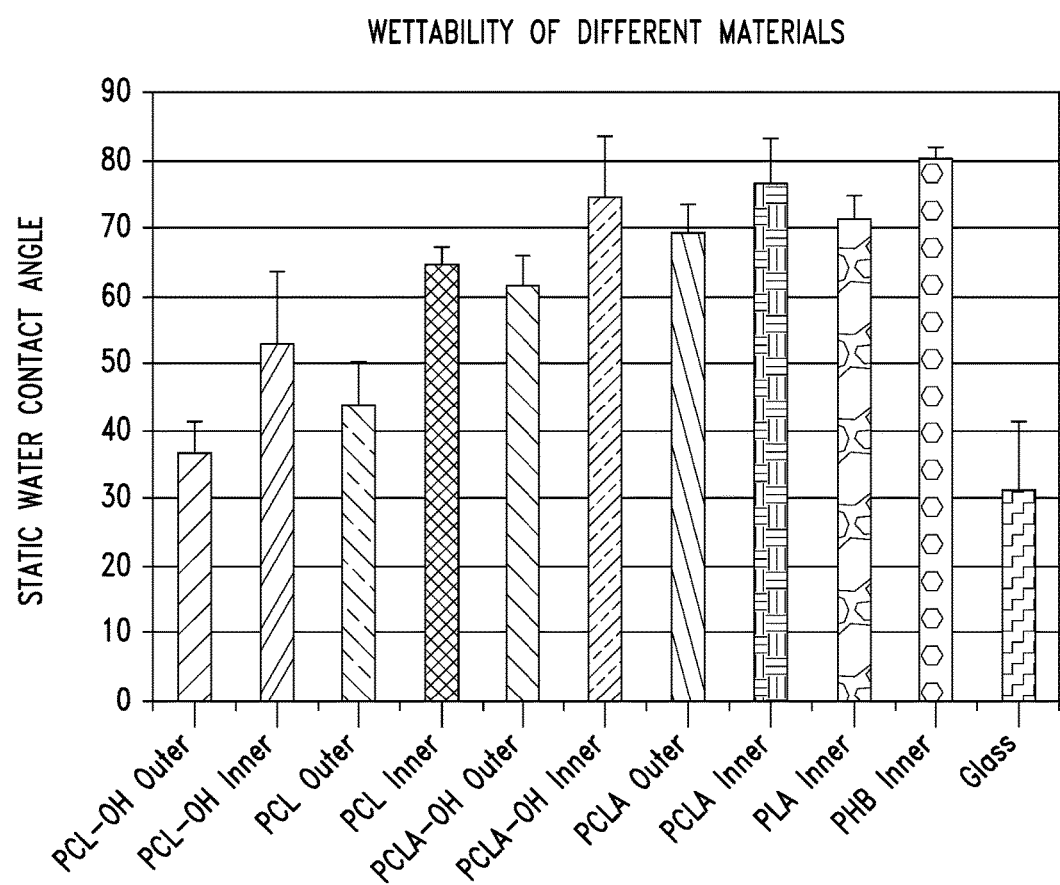
FIG. 6 shows a graph of wettability data for a number of different materials formed as films.

The results are graphed in FIG. 6.

The results show that the smooth outer surface is more hydrophilic than the porous inner surface and that NaOH treated materials are more hydrophilic than the untreated counterparts. Also that PCL is more hydrophilic than the PCLA composite either before or after the NaOH treatment.

For comparison, the wettability of Poly(3-hydroxybutyrate) (PHB) was tested. PHB (Astra Tech, Sweden) was dissolved into chloroform at 70° C. and then applied evenly onto the surface of glass slides. PHB (1% wt/v) film had a contact angle of 80.03°.

Mechanical Testing

The tensile strength, Young's modulus and maximum strain of PCL and PCLA films were measured, before and after NaOH treatment.

Tensile strength is defined as the maximum amount of tensile stress that a material can be subjected to before failure. Young's modulus is a measurement of stiffness. Maximum strain is measured as the total elongation per unit length of material subject to same applied stress.

Tensile strength, Young's modulus and maximum strain were measured on a mechanical tensile tester (Instron 1122) at 23±1° C., 50%±2% relative humidity. The cross sectional area was (3.8×0.06) mm$^2$; grip distance was 35 mm; strain rate was set at 50 mm/min and the full scale load 0.005 KN.

Young's modulus was measured from the initial slopes in the elastic region and the tensile strength was the average of ultimate stress at the breaking point of the films.

The results are set out in Table 3.

TABLE 3

Mechanical strength of PCL and PCL + PLA (=PCLA) films, before and after NaOH treatment.

| Samples (3% weight/volume) | Thickness (μm) | Max. STR. (MPa) | Max. STN. (mm/mm) | Young's Modulus (MPa) |
|---|---|---|---|---|
| PCL | 0.057 | 16.3 | 7.67 | 115.48 |
| PCL (NaOH treated) | 0.054 | 14.98 | 7.14 | 118.89 |
| PCL + PLA | 0.053 | 11.59 | 2.86 | 175.52 |
| PCl + PLA (NaOH treated) | 0.053 | 10.73 | 2.44 | 156.48 |

The results show that mechanical strength of the PCLA film is lower than that of the PCL film. It is expected that the PCLA film will have a faster degradation rate than the PCL film. Thus, the inclusion of 20 wt % PLA has modified the mechanical properties of PCL and provides a favourable balance in terms of handling ex vivo (e.g. by a surgeon) and performance in vivo.

The results also show that PCL films (with or without a PLA component) can be fabricated at micro-thickness and at the same time retain mechanical strength and flexibility.

Cell Compatibility Analysis
Cell Source

The NG108-15 cell line was purchased from ECACC (Porton Down, UK). Schwann cells were isolated from neonate rats as previously described [3] and maintained with 63 ng/ml glial growth factor (GGF) and 10 µM forskolin mitogen supplemented media.

Cell Culture

NG108-15 cells were maintained in DMEM (Dulbecco's Modified Eagle's Medium), containing 4.5 g/L glucose; 5% foetal bovine serum; 1% antibiotics, and supplemented with 1×HAT (a liquid mixture of sodium hypoxanthine, aminopterin and thymidine) solution, at 37° C. in a 5% $CO_2$ humidified atmosphere.

Schwann cells were cultured in DMEM containing 10% serum and antibiotics (penicillin 100 IU/ml and streptomycin 100 µg/ml).

Cell Attachment Analysis 1 ml of NG108-15 cells ($10^5$/ml) were seeded onto PCL and/or PCLA films (3.14 $cm^2$) and cultured for 3 hours at 37° C. in a 5% $CO_2$ humidified atmosphere.

For the MTS assay, films were transferred into fresh cell culture plates and washed gently twice in 37° C. cell culture medium to ensure that only attached cells were tested. The CellTiter 96® Aqueous One Solution Cell Proliferation Assay (MTS) (Promega UK) is a colorimetric method for determining the number of viable cells. The active component is a tetrazolium compound called MTS which is reduced by cells to a colored formazan product. The amount of formazan product is directly proportional to the number of living cells; therefore, cell proliferation or death can be quantified by reading the plate at 490 nm.

DNA assay for the attachment of NG108-15 cells was conducted using the Hoechst stain reagent (Hoechst 33258 from Sigma-Aldrich), which specifically binds onto DNA and as such can be used to detect the contents of a sample DNA by plotting a standard emission-to-content curve. After 3 hours of culturing films were washed twice in PBS followed by three freeze and thaw cycles in $dH_2O$ to release the DNA from cells. FLUOstar OPTIMA fluorescence microplate reader was used to measure the fluorescence.

Figure 7:
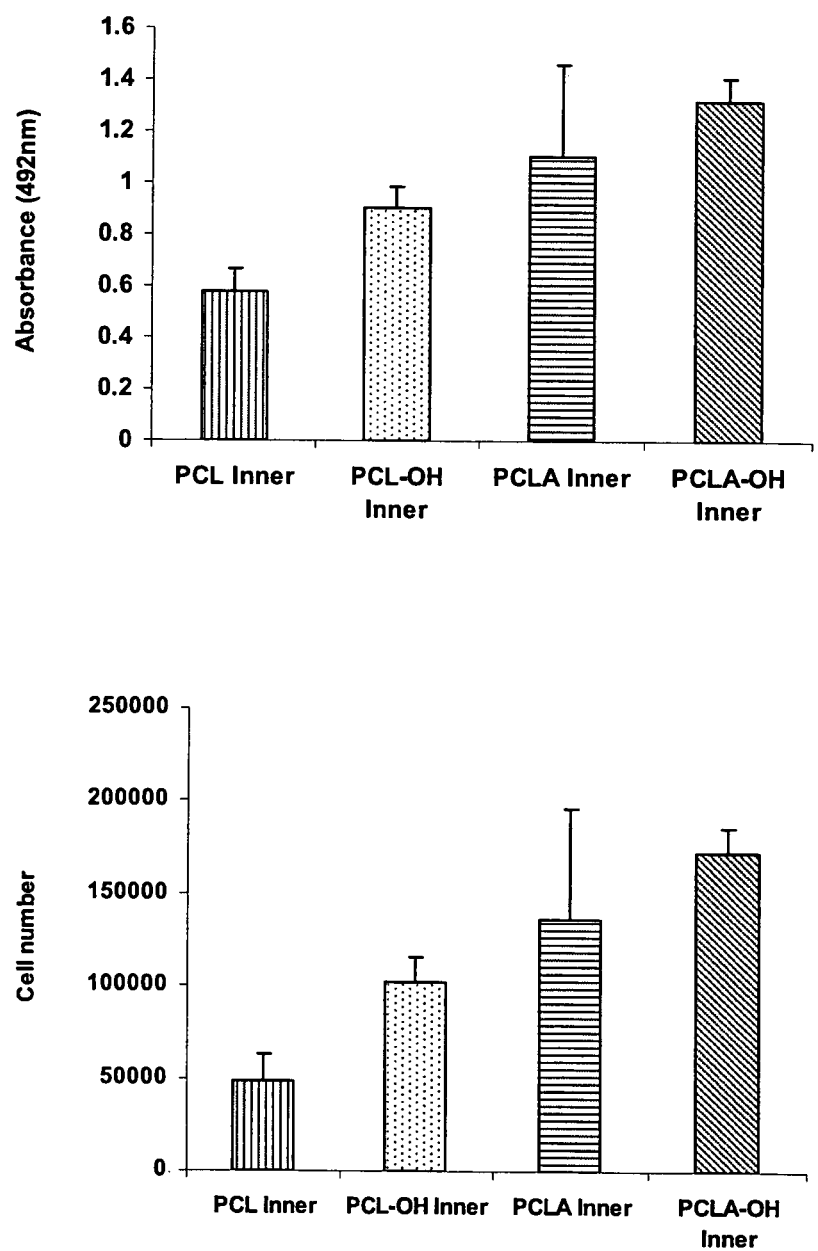
FIG. 7 shows a graph of MTS cell attachment data for NG108-15 cells on different materials.

The results of the MTS analysis are shown in FIG. 7. FIG. 7A shows measured absorbance for the inner surfaces of PCL and PCLA films, with and without NaOH treatment. FIG. 7B shows cell number for the inner surfaces of PCL and PCLA films, with and without NaOH treatment.

The results show that NaOH treated materials are more compatible with NG108-15 cells than untreated materials. This is quantified in Table 4, which provides the ratio (as a %) of the cell attachment achieved with untreated material compared to treated material.

TABLE 4

Comparison of NG108-15 cell attachment on NaOH treated and untreated PCL and PCLA films (inner surface).

| Samples | 2 hour | 3 hour | 4 hour |
|---|---|---|---|
| PCL/NaOH treated PCL | 39.6% | 45.7% | 47.5% |
| PCLA/NaOH treated PCLA | 66.9% | 77.5% | 84.9% |

The data obtained is in keeping with the results from DNA attachment analysis, discussed below.

Figure 8:
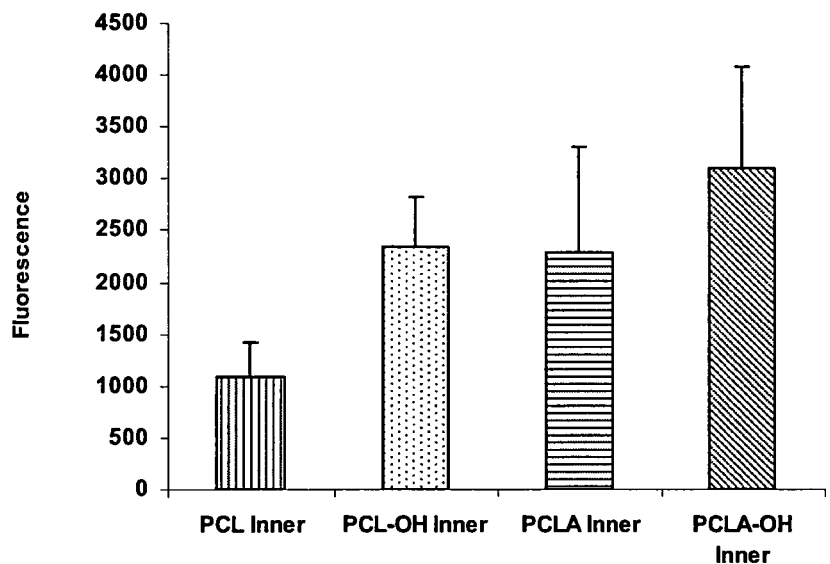
FIG. 8 shows a graph of DNA cell attachment data for NG108-15 cells on different materials.
Figure 8:
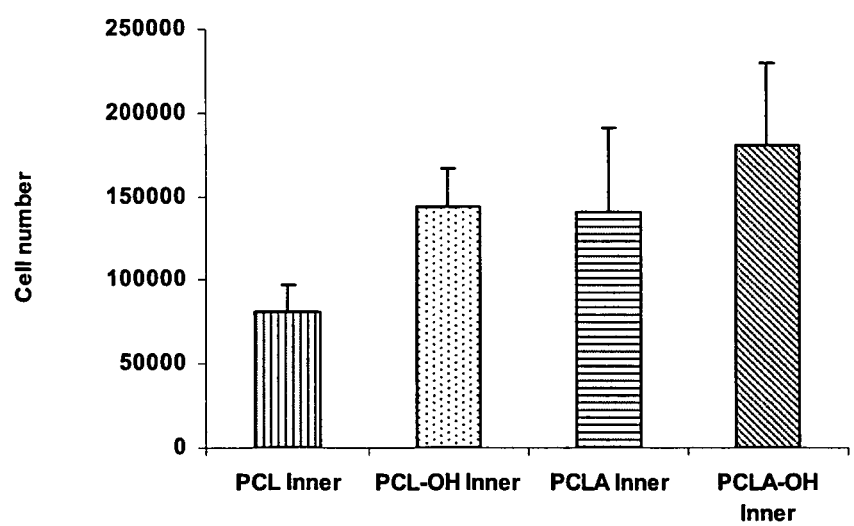

The results of the DNA (Hoechst) analysis are presented in FIG. 8. The results show that NaOH treated materials are more compatible with NG108-15 cells than untreated ones and the NaOH treated pitted surface of PCLA showed the best result. These results confirmed those of the MTS assay.

Cell Proliferation Analysis

The proliferation rate of NG108-15 cells on PCL and PCLA films (both NaOH treated and untreated) was also analyzed using the MTS method. NG108-15 cells (5000/$cm^2$) were seeded onto films in each well of the 12-well plate and cultured as described above. Another resorbable biomaterial, poly(D,L-lactic acid) (PLA) was included as a comparison.

Figure 9:
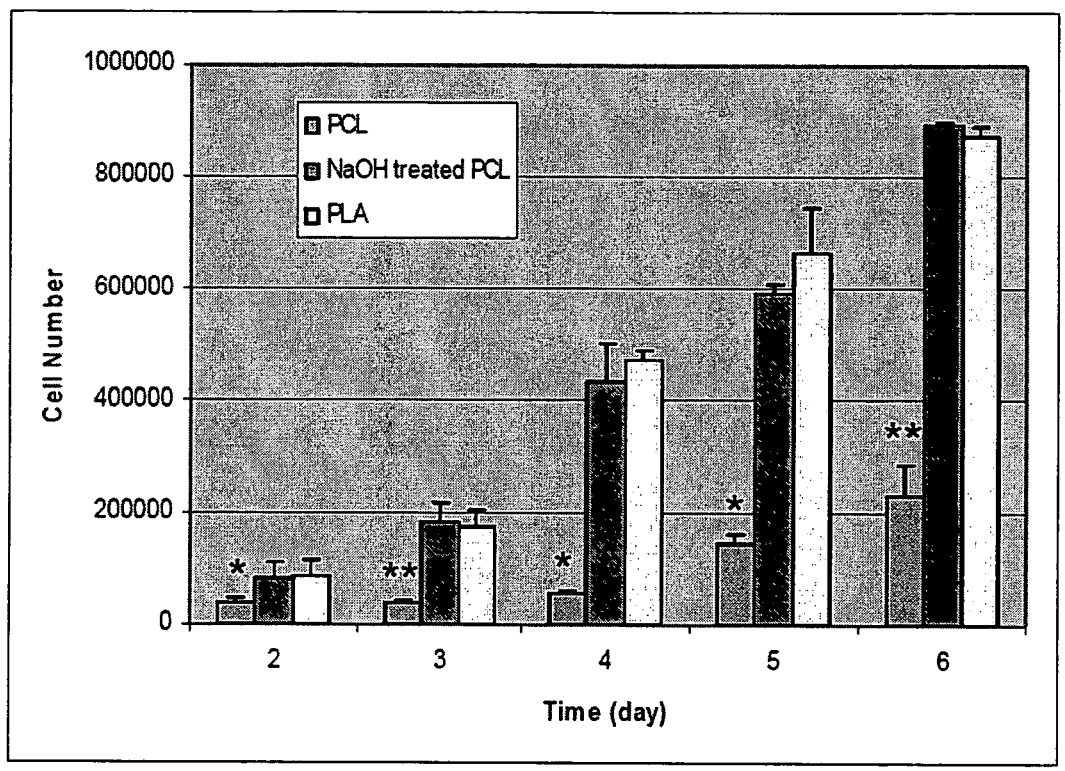
FIG. 9 shows a graph of proliferation data for NG108-15 cells on untreated PCL films; NaOH treated PCL films, and PLA.

The results are provided in FIG. 9. The results show that in six days cell number increased approximately 9 fold on PLA films and NaOH treated PCL films. The effect of NaOH treatment on the PCL film is remarkable and demonstrates that NaOH treatment of PCL provides a surface having a significantly enhanced compatibility for peripheral nerve cells and provides an "active" environment that encourages peripheral nerve cell proliferation.

Figure 10:
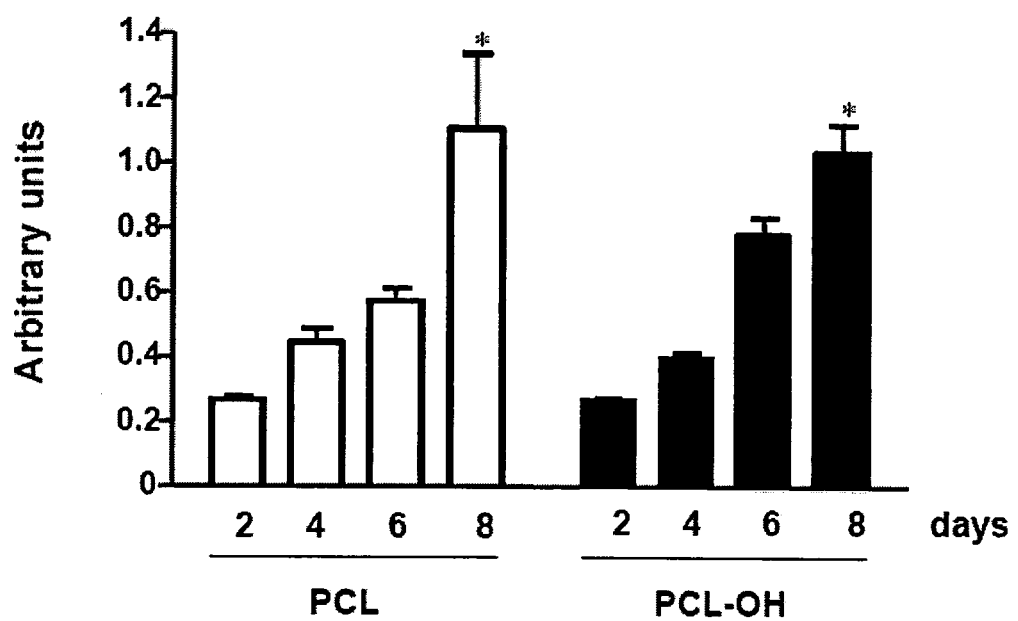
FIG. 10 shows the results of Schwann cell proliferation on treated and untreated PCL films.

Schwann cell proliferation was also studied using the MTS method. Schwann cells were grown on NaOH treated and untreated PCL films cast from DCM. 6000/$cm^2$ cells were seeded onto the surface of PCL and NaOH-treated PCL films. Cells were cultured in DMEM containing 10% serum and antibiotics (penicillin 100 IU/ml and streptomycin 100 µg/ml). Cell culturing was conducted for 8 days; readings were taken on every second day (antibody staining was carried out after 7 days of culturing; see below). The results were graphed in FIG. 10. The results show that Schwann cells proliferate on PCL regardless of whether or not there has been hydroxide treatment.

Figure 11:
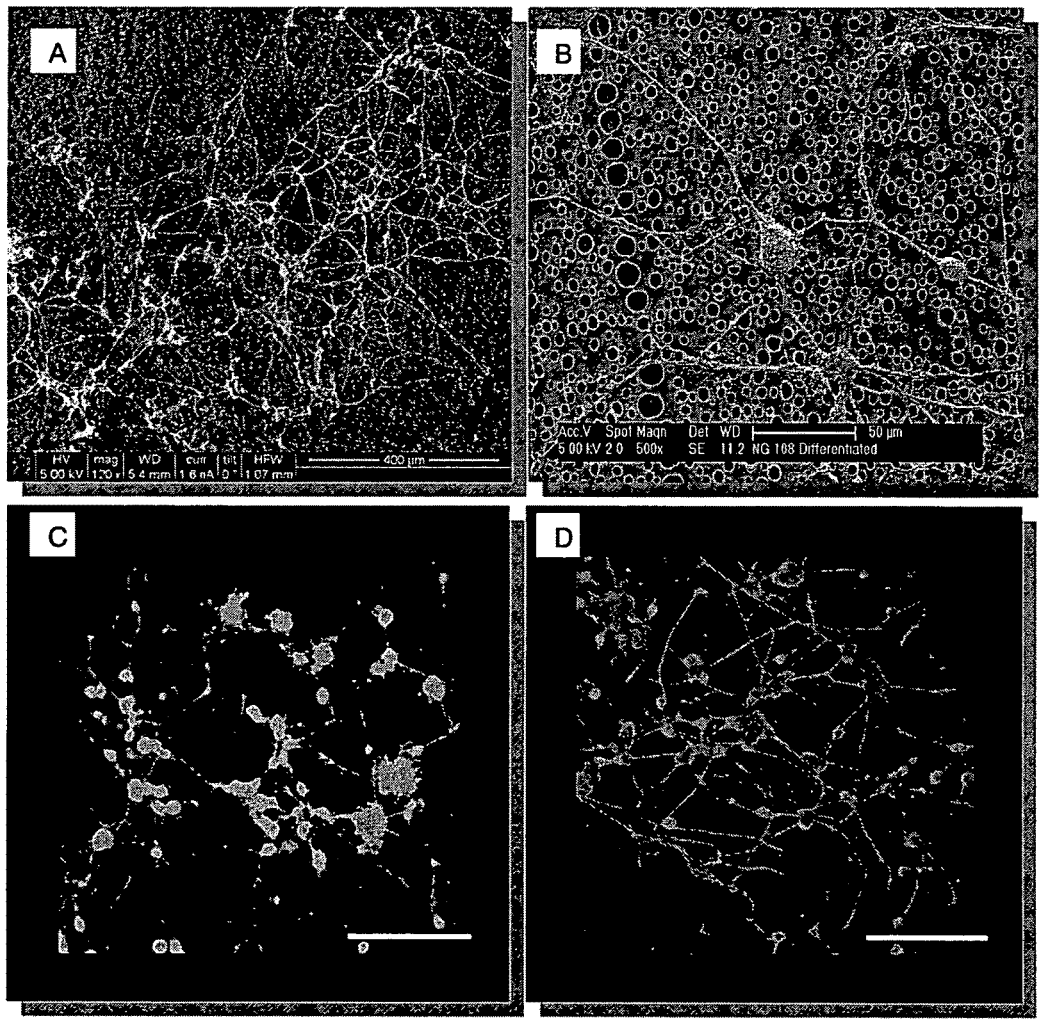
FIG. 11 shows (A) an SEM image of differentiated NG108-15 cells on NaOH treated PCL film; (B) SEM image of (A) at higher resolution; (C) Confocal microscope image of phalloidin stained cells; (D) Confocal microscope image of anti-neurofilament antibody stained cells. Bar=100 μm in (C) and (D).

In vitro testing showed that the PCL and PCLA films, with and without hydroxide treatment, supported the attachment and proliferation of both NG108-15 cells and Schwann cells, which are involved in maintenance of axons and are crucial for neuronal survival and regeneration. Importantly, NG108-15 cells could also be induced into differentiated phenotype with long branched neurites extending across the surface of the material. FIGS. 11A and 11B show the differentiated NG108-15 cells branching and extending over the pitted PCL surface. FIG. 11C shows phalloidin stained cells and FIG. 11D shows anti-neurofilament antibody stained cells, which confirms proper differentiation. The excellent neurite elongation and branching indicates good cell-material compatibility.

Figure 12:
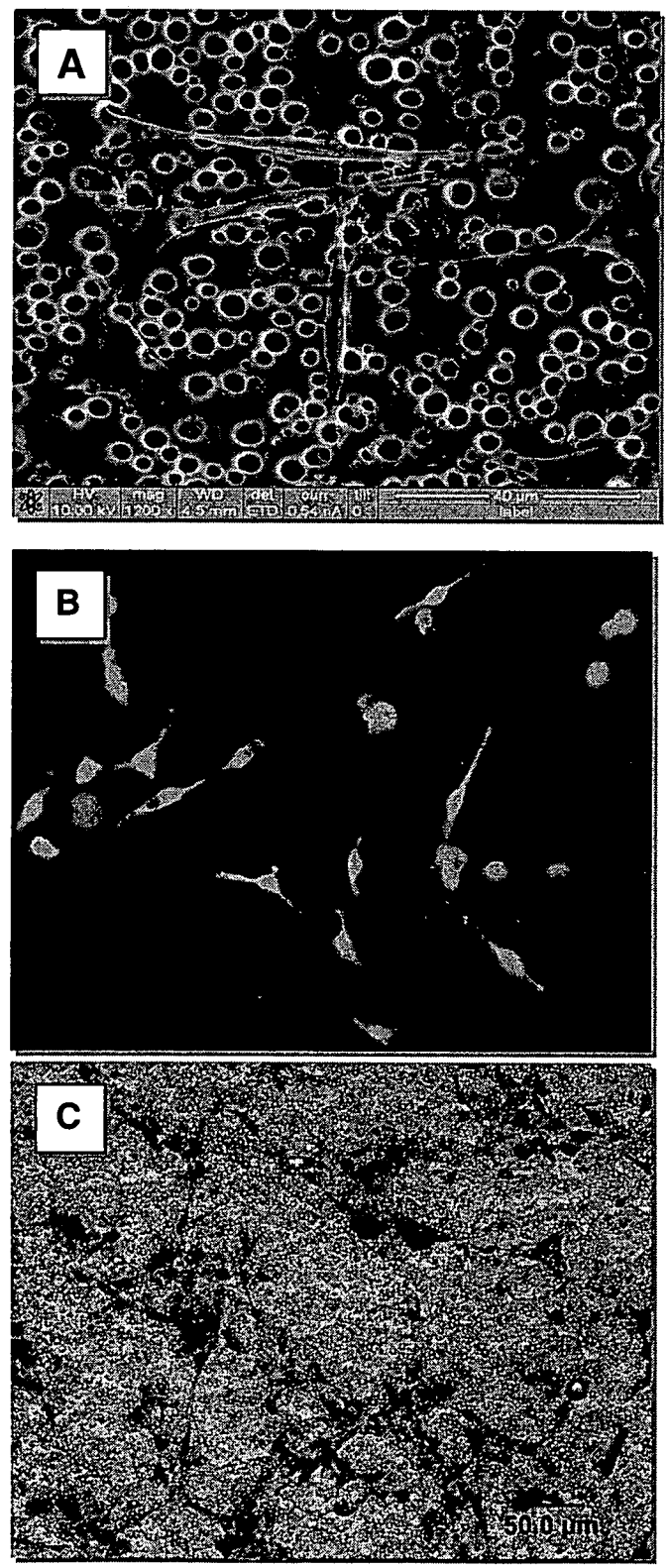
FIG. 12 shows (A) an SEM image of Schwann cells growing on NaOH treated PCL film; (B) Immunohistochemical-stained cells, using antibody against marker protein S100; (C) Toluidine Blue O stained Schwann cells.

FIGS. 12A to C show Schwann cell growth on the NaOH treated PCL film. FIG. 12A shows a typical bipolar spindle-shaped phenotype. The immunohistochemical-stained cells shown in FIG. 12B confirms expression of marker protein and this together with the Toluidine Blue O stained cells of FIG. 12C indicates excellent cell-material compatibility.

Haematoxylin Staining

Figure 13:
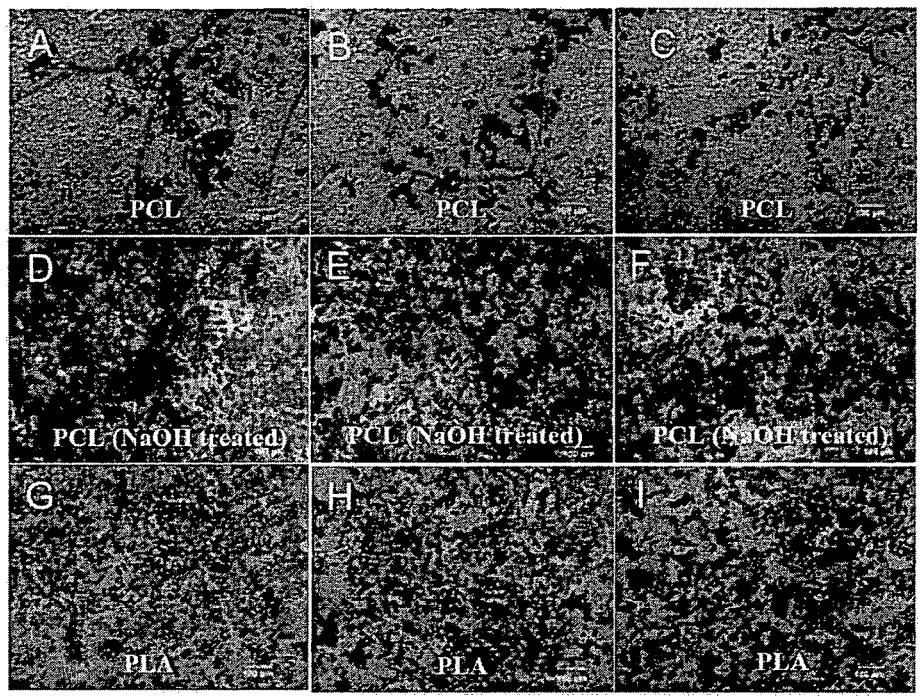
FIG. 13 shows images of haematoxylin stained nuclei of NG108-15 cells on different materials.

Images of haematoxylin stained nuclei of NG108-15 cells on PCL films, NaOH treated PCL films and PLA films (reference) were obtained after 5 days in culture. The images are shown in FIG. 13. For each material, experiments were carried out in triplicates and repeated three times.

As can be seen from FIG. 13, there is excellent reproducibility between each of the 3 films for each material. Furthermore, good levels of cell proliferation are seen for PCL. Most impressive is the result provided by NaOH treated PCL where surprisingly high levels of cell proliferation were observed. Furthermore, the cells are distributed evenly on the surface.

Nerve Re-Growth—in vivo

NaOH treated PCL films were cut into rectangular sheets and rolled around a 16G intravenous cannula (16G Abbocath®-T, Abbott Ireland, Sligo, Republic of Ireland). The standardised internal diameter of the conduits is 1.6 mm, more than 1.5 times the diameter of rat sciatic nerve, thus allowing space for post-injury swelling. Conduits were sealed by controlled heating at 60° C. while still mounted on the cannula. Prior to surgical implantation, the conduits were sterilised using UV radiation.

All work was conducted in keeping with the terms of the Animals (Scientific Procedures) Act 1986, and the experimental design recognised the need to optimise animal welfare.

Eight-week-old female adult Sprague-Dawley rats (Harlan, Inc. USA) (weighing between 180-220 g) were anesthetised with isofluorane (Abbott Laboratories Ltd.). The site for implantation was shaved and sterilised with surgical alcohol. The left sciatic nerve of the rat was exposed through a gluteal muscle-splitting incision at the mid-thigh level after a dorsolateral skin incision and splitting of the fascia between the gluteus and biceps femoris muscle. The surrounding tissues were separated and a piece of 8 mm in length was removed from the sciatic nerve, leaving a 10-mm nerve gap after retraction of both ends.

Figure 14:
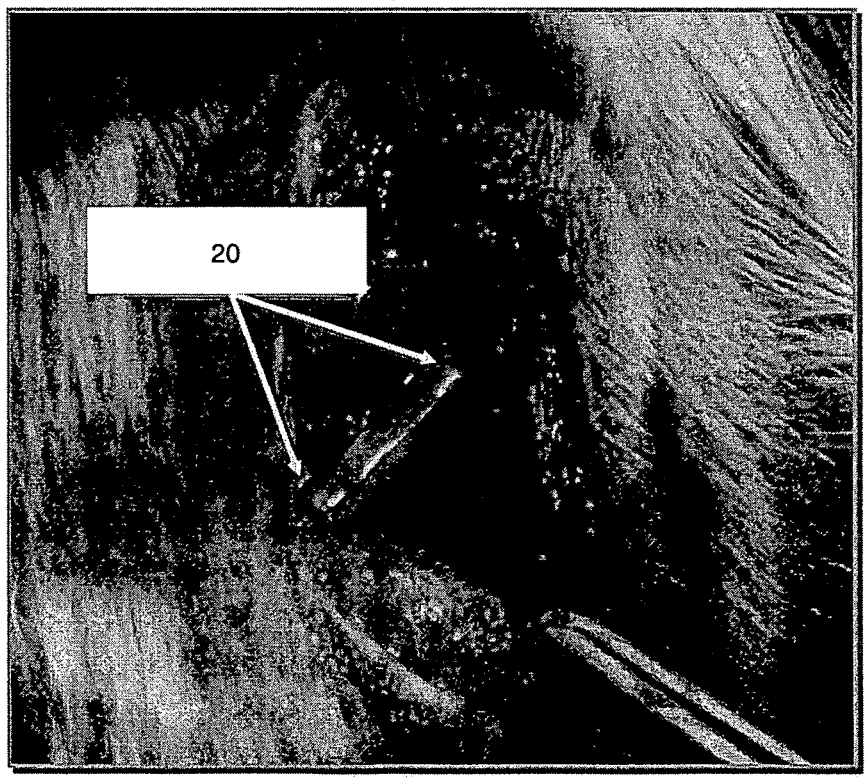
FIG. 14 shows a photograph of a PCL conduit sutured in place to bridge a 10 mm nerve gap.

Under an operating microscope (Zeiss®, Germany), the proximal and distal nerve stumps of the transected nerve were secured epineurially within the 14 mm long guidance conduit using a 9-0 ETHILON suture. Both the nerve ends were positioned 2 mm from the conduit ends to ensure the proximal and distal nerve stumps were separated by a 10 mm gap (20, FIG. 14). A single 4-0 coated VICRYL was used to suture the muscle and skin. After the operation, 4 μg of buprenorphine (20 μg/kg) was injected into the rats as an analgesic intramuscularly. The depth of anaesthesia, heart rate and breathing were checked periodically to ensure the rat was in a good surgical condition. A total of 9 animals were implanted in the same manner. The animals were caged in a temperature- and humidity-controlled room with a 12-hour light/dark cycle. Food and water was provided immediately.

Figure 15:
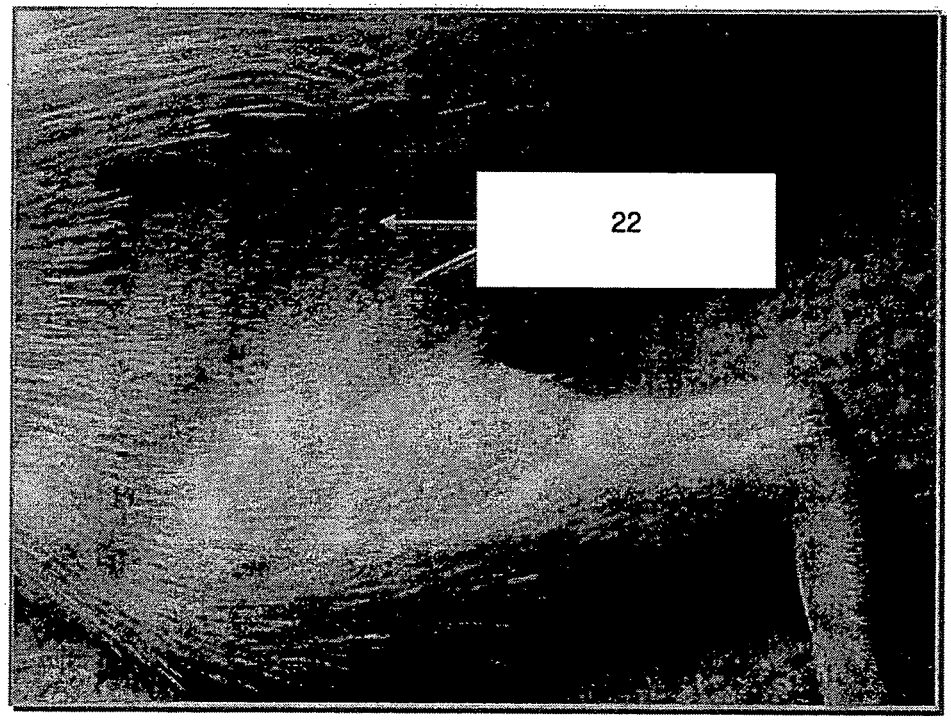
FIG. 15 shows a photograph of the healed wound of a rat 14 days/2 weeks after surgery.
Figure 16:
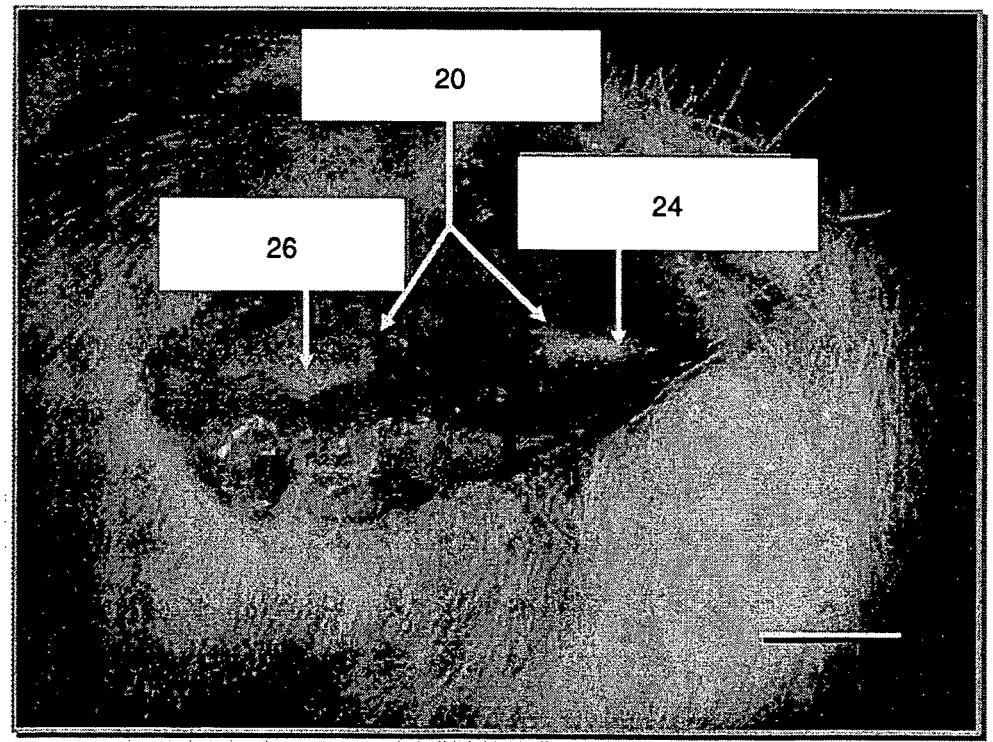
FIG. 16 shows a photograph of a PCL conduit 14 days/2 weeks after implantation.

14 days/2 weeks post-operation, the site was well-healed without any sign of swelling and inflammation (22, FIG. 15). The animals were killed using Schedule I method. FIG. 16 shows that the conduit 20 was integrated with both proximal 24 and distal 26 stumps of the natural nerve. No severe inflammatory response was found in all nine animals. The conduits didn't open or collapse in all samples (n=9). (FIG. 16, Bar=10 mm).

Figure 17:
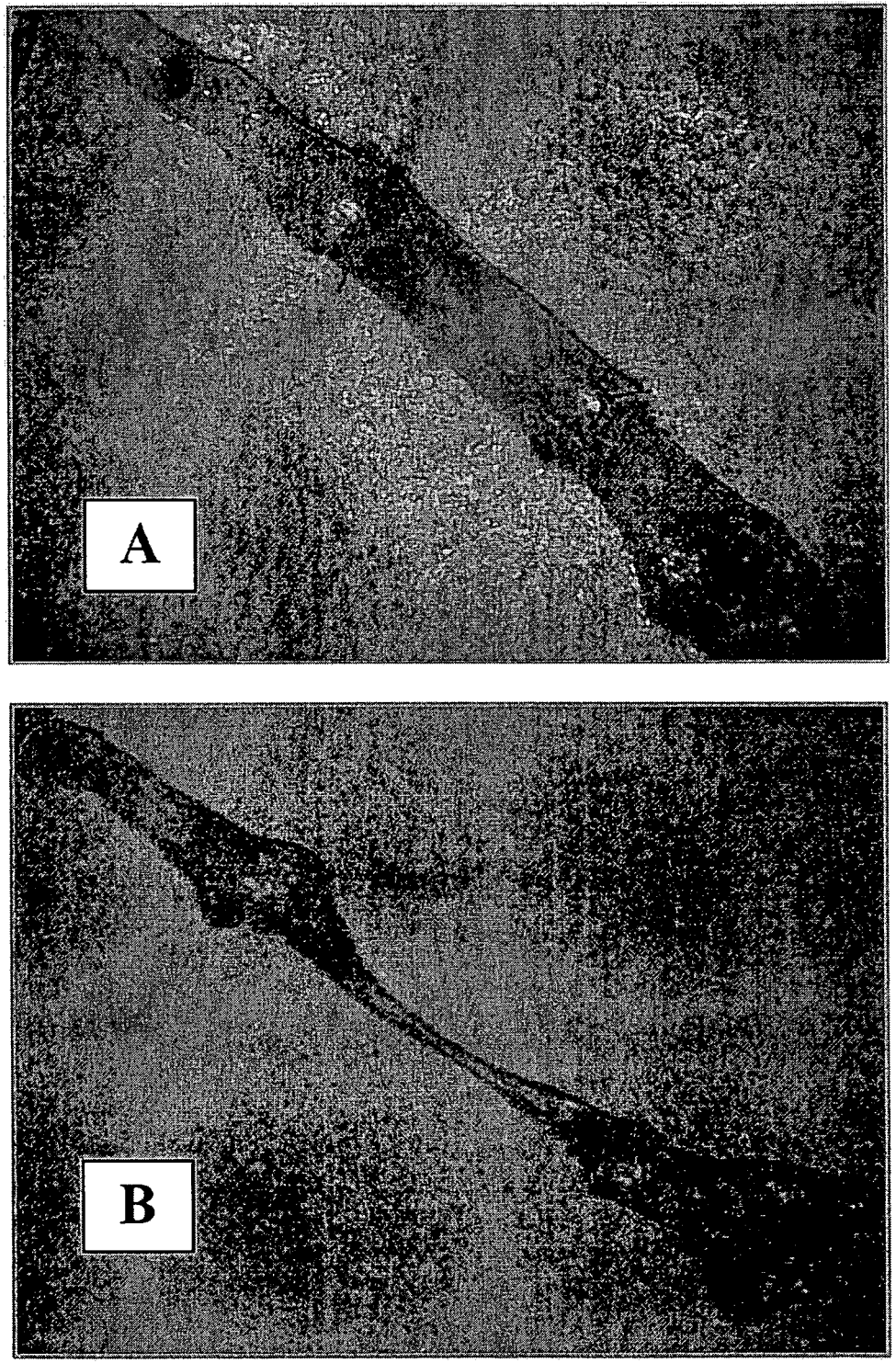
FIG. 17 shows photographs of a harvested PCL nerve conduit after 14 days/2 weeks of in vivo testing (A) and regenerated nerve tissue after the removal of the PCL conduit (B)

FIG. 17A shows the harvested PCL peripheral nerve conduit after 14 days of in vivo testing. FIG. 17B shows the regenerated nerve tissue after the removal of PCL conduit.

For immunohistochemical studies, the entire implants with a 2 mm length of proximal and distal nerve were harvested en bloc, pinned onto a plastic card to avoid shrinkage and marked at the proximal end. Fixation was carried out in 4% (wt/v) paraformaldehyde solution for 24 h at 4° C. and then washed three times with phosphate buffered saline (PBS) containing 15% sucrose and 0.1% sodium azide.

Blocks for cryostat sectioning were prepared by rapid freezing of samples into OCT™ mounting medium in liquid nitrogen. Systematic longitudinal 15 μm transversal sections were cut using Bright (Model OTE) cryostat instrument at −23° C. and collected onto glass slides coated with Vectabond (Vector Laboratories). Samples were dried overnight in 37° C. oven. Immunostaining was performed by using polyclonal rabbit antibodies directed against protein gene product (PGP9.5) (Dako, dilution 1:200) in order to identify neurites. Schwann cells were identified using polyclonal rabbit anti-protein S100 (Dako, dilution 1:500). Secondary antibody used in the staining was FITC conjugated anti-rabbit IgG (Vector labs, F1-1000; 1:100).

Schwann Cell Detection (Immunostaining)

Figure 18:
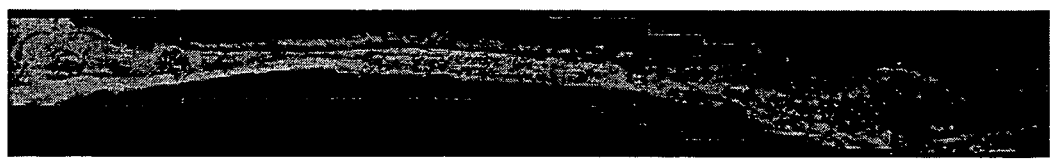
FIG. 18 shows photographs of peripheral nerve regrowth in the conduit of FIG. 17, being anti-PGP9.5 antibody stained regenerated nerve fibres (18A) and anti-S100 antibody stained Schwann cells (18B)
Figure 18:
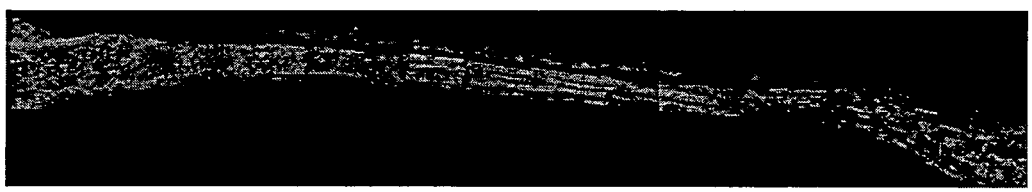

FIG. 18 shows the results of immuno-staining of neurofilament and Schwann cells in the PCL conduit used in the in vivo testing discussed above.

FIG. 18A shows anti-PGP9.5 antibody stained neurofilaments and FIG. 18B shows anti-S100 antibody stained Schwann cells.

The results of the preclinical testing show that the regenerating neurites have grown through the whole length (i.e. 10 mm) of the conduit together with the infiltrated Schwann cells.

In contrast, the results reported in [1] (using the same preclinical testing method) show that only a much smaller extent of nerve re-growth was achieved when a PHB conduit is used. The effect of fibrin matrix (Tisseel®) and Schwann cells (SC)/differentiated mesenchymal stem cells (dMSC) on the regeneration of peripheral nerves in PHB conduits is shown in Table 5. PHB conduits were used to bridge a 10 mm gap in the left sciatic nerve of adult Sprague-Dawley rats (Harlan Inc. USA). Regeneration was analysed by immunohistochemical staining to identify PGP9.5 for neurofilament and S100 for Schwann cells two weeks post-implantation.

The results from [1] are set out in Table 5 below.

TABLE 5

PHB conduits filled with fibrin gel matrix and/or cells were used to bridge a 10 mm gap in the left sciatic nerve of adult Sprague-Dawley rats.

| Antibodies used for immunohistochemical staining | | Empty PHB conduit | PHB with fibrin matrix | PHB with fibrin matrix-dMSC | PHB with fibrin matrix-SC |
|---|---|---|---|---|---|
| PGP9.5 | | 1.91 mm* | 2.28 mm* | 3.16 mm* | 3.17 mm* |
| S100 | Proximal | 2.2 mm | 2.4 mm | 3.30 mm* | 3.40 mm* |
| | Distal | 1.7 mm | 2.1 mm | 2.80 mm* | 2.91 mm* |

*Numbers in bold were accurate data from the original work in [1]. The other four measurements were extracted from the figure in [1].

It is clear from the above results that the PCL scaffold of the present invention is an "active" scaffold in that it encourages and promotes peripheral nerve growth.

Figure 19:
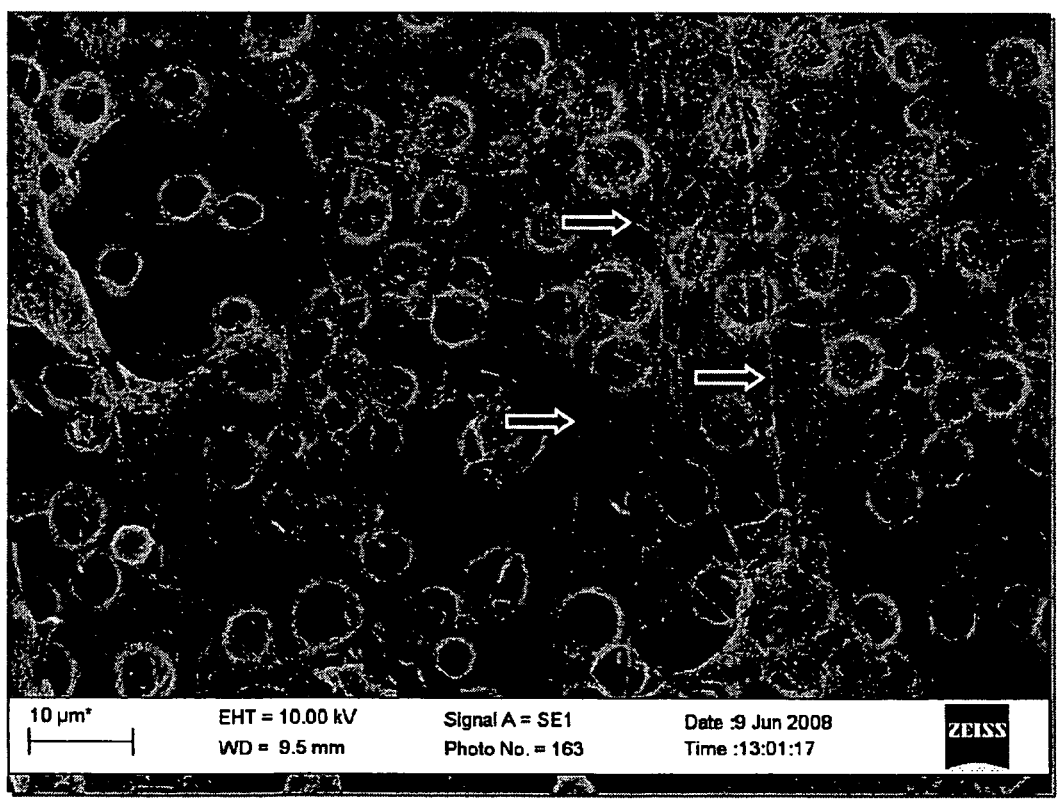
FIG. 19 shows an SEM image of the inner surface of a PCL conduit after 14 days/2 weeks in vivo.

FIG. 19 shows an SEM image obtained for the inner (luminal) surface of a PCL conduit after 14 days/2 weeks in vivo. The arrows are pointing at the regenerated nerve fibres. The SEM image also serves to show that the pitted surface morphology was not affected by the heat sealing method used to the form the conduit.

18 Week in vivo Study

A 1 cm sciatic nerve gap in adult Sprague-Dawley rats was created and repaired with either NaOH treated PCL conduits or a nerve autograft (9 subjects in each group).

In both groups, 3 rats were prematurely culled due to autotomy, a commonly reported phenomenon occurring as a result of the surgical procedure.

The remaining 6 rats in each group adopted a normal living style without any visible difference in behaviour. Before sacrifice, the rats treated with PCL conduits were observed to support themselves on both hind-limbs, indicative of significant distal regeneration. This was supported by electrophysiological measurements.

Briefly, after induction of anaesthesia (week 18), the sciatic nerves were exposed from the sciatic notch to the distal branches emanating from the popliteal fossa. A stimulating electrode was placed in the proximal nerve segment and a recording electrode distal to the repair site. In response to the electrical stimulation, we were able to record action potentials (nerve conduction) in the sural, medial gastrocnemius and tibial nerve branches indicating significant regeneration across the nerve conduit and distal towards the end organs.

Reinnervation of hind-limb muscles was indicated by recovery of gastrocnemius muscle weight. In previous studies of nerve repair, we have shown that peak muscle atrophy (loss of weight) occurs at 7 weeks post-injury. At this time point, muscle weight on the operated side was 27.87±3.04% of the contra-lateral side.

However, 18 weeks after repair with the PCL conduits, the muscle weight was significantly ($P<0.05$) increased to 44.64±4.67% and to 61.37±2.37% ($P<0.01$) with autografts. These results indicate the capacity of the PCL nerve conduit to support nerve regeneration and reinnervation comparable to the gold standard nerve autograft.

It is to be understood that variants of the above described examples of the invention in its various aspects, such as would be readily apparent to the skilled person, may be made without departing from the scope of the invention in any of its aspects.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

[1] Kalbermatten, D. F. et al., "Fibrin matrix for suspension regenerative cells in an artificial nerve conduit", Journal of Plastic, Reconstructive & Aesthetic Surgery (2008), Volume 61, Issue 6, Pages 669-675.

[2] Rasband, W. S., Image J, U. S. National Institutes of Health, Bethesda, Md., USA, http://rsb.info.nih.gov/ij/, 1997-2008.

[3] Caddick, J. et al., "Phenotypic and functional characteristics of mesenchymal stem cells differentiated along a Schwann cell lineage", *Glia* 54 (2006), pp. 840-849.

The invention claimed is:

1. A peripheral nerve growth conduit including poly-ε-caprolactone (PCL) and poly-lactic acid (PLA), wherein the weight ratio of PCL:PLA is in the range 20:1 to 2:1, wherein the conduit comprises a conduit wall having a thickness, and wherein the conduit wall does not include any pores extending through the thickness of the conduit wall, and wherein the conduit wall defines a luminal space and provides an inner surface of PCL and PLA for attachment of peripheral nerve cells.

2. The peripheral nerve growth conduit according to claim 1, wherein the inner surface of the conduit comprises pits and wherein the pits have an average diameter in the range 1-10μm.

3. The peripheral nerve growth conduit according to claim 2, wherein the pits have an average depth in the range 1-4μm.

4. The peripheral nerve growth conduit according to claim 2, wherein the pits cover the inner surface at a % surface coverage of 45% to 55%.

5. The peripheral nerve growth conduit according to claim 1 wherein the conduit comprises at least 75 wt % PCL based on the total weight of the conduit.

6. The peripheral nerve growth conduit according to claim 1, wherein the PCL has a number average molecular weight in the range 60,000 to 100,000 g/mol.

7. The peripheral nerve growth conduit according to claim 1, wherein the conduit is a tubular conduit and the thickness of the conduit walls is in the range 20μm to 80μm.

8. The peripheral nerve growth conduit according to claim 1, wherein the conduit has a length in the range 5 mm to 20 mm.

9. The peripheral nerve growth conduit according to claim 1, wherein the conduit has a diameter in the range 1 to 5 mm.

10. The peripheral nerve growth conduit according to claim 1, wherein the conduit is made from a film comprising PCL, by solvent evaporation and optionally opposite edges of the film are joined together by heat sealing to form the conduit.

11. The peripheral nerve growth conduit according to claim 1, wherein the inner surface of the conduit has been treated with an alkaline composition, wherein the duration of the treatment with alkaline composition is in the range 30 minutes to 3 hours, the alkaline composition is aqueous NaOH, and the concentration of the aqueous NaOH is in the range of 8N to 12N.

12. The peripheral nerve growth conduit according to claim 1, wherein the inner surface of the conduit includes —COOH and/or —OH terminated PCL chains, and the conduit has nanopits on the inner luminal surface of the conduit.

13. The peripheral nerve growth conduit according to claim 1, wherein the inner surface of the conduit has an average surface roughness (Ra) of at least 1 μm.

14. The peripheral nerve growth conduit according to claim 1, wherein a surface roughness of an outer surface of the conduit has an average surface roughness (Ra) of less than 1 μm.

15. The peripheral nerve growth conduit according to claim 1, wherein the difference in average surface roughness between the inner surface and an outer surface is at least 1 μm.

16. A kit for treating a peripheral nerve in a human or animal, the kit including a peripheral nerve growth conduit according to claim 1.

17. A method of treating a damaged peripheral nerve utilizing.

18. A method of making a peripheral nerve growth conduit according to claim 1, the method comprising the step of:
  i) forming a film by solvent-casting a solution including PCL, PLA and a solvent, wherein the weight ratio of PCL: PLA is in a range 20:1 to 2:1, and allowing the solvent to evaporate; and
  ii) joining opposite edges of the film together by heat sealing to form the conduit.

19. The peripheral nerve growth conduit according to claim 1, wherein the weight ratio of PCL: PLA is in a range of 10:1 to 2:1.

20. The peripheral nerve growth conduit according to claim 1, wherein the PLA is provided as a blend with the PCL.

21. A peripheral nerve growth tubular conduit including poly-ε-caprolactone (PCL), an inner surface of the conduit comprising pits, wherein the conduit comprises at least 50 wt % PCL based on the total weight of the conduit and the PCL has a number average molecular weight in the range 60,000 to 100,000 g/mol, and wherein the conduit has a length in the range 5 mm to 50 mm and a diameter in the range 1 to 5 mm, and wherein the peripheral nerve growth conduit further including poly-lactic acid (PLA), wherein the weight ratio of PCL:PLA is in the range 20:1 to 2:1, wherein the conduit comprises a conduit wall having a thickness, and wherein the conduit wall does not include any pores extending through the thickness of the conduit wall.

22. A peripheral nerve growth conduit including poly-ε-caprolactone (PCL) and poly-lactic acid (PLA), wherein the weight ratio of PCL:PLA is in the range 20:1 to 2:1 wherein the conduit comprises at least 50 wt % PCL based on the total weight of the conduit, wherein the conduit comprises a conduit wall having a thickness, and wherein the conduit wall does not include any pores extending through the thickness of the conduit wall.

* * * * *